United States Patent
Esenaliev et al.

(10) Patent No.: US 6,498,942 B1
(45) Date of Patent: Dec. 24, 2002

(54) OPTOACOUSTIC MONITORING OF BLOOD OXYGENATION

(75) Inventors: Rinat O. Esenaliev, Gavlveston, TX (US); Massoud Motamedi, Houston, TX (US); Donald S. Prough, Galveston, TX (US); Alexander A. Oraevsky, Houston, TX (US)

(73) Assignee: The University of Texas System, Austin, TX (US)

( * ) Notice: Subject to any disclaimer, the term of this patent is extended or adjusted under 35 U.S.C. 154(b) by 4 days.

(21) Appl. No.: 09/633,597

(22) Filed: Aug. 7, 2000

Related U.S. Application Data

(60) Provisional application No. 60/147,577, filed on Aug. 6, 1999.

(51) Int. Cl.$^7$ ............................................ A61B 5/00
(52) U.S. Cl. ..................... 600/310; 600/322; 600/323
(58) Field of Search ........................ 600/309–310, 600/322–325, 327, 332, 339, 341–343

(56) References Cited

U.S. PATENT DOCUMENTS

| | | | |
|---|---|---|---|
| 4,028,933 A | 6/1977 | Lemons et al. | 73/67.6 |
| 4,212,206 A | 7/1980 | Hartemann et al. | 73/606 |
| 4,430,897 A | 2/1984 | Quate | 73/606 |
| 4,710,030 A | 12/1987 | Tauc et al. | 356/432 |
| 4,727,420 A | 2/1988 | Kohda et al. | 358/112 |
| 4,953,539 A * | 9/1990 | Nakamura et al. | 600/109 |
| 5,041,121 A | 8/1991 | Wondrazek et al. | 606/128 |
| 5,136,172 A | 8/1992 | Nakata et al. | 250/572 |
| 5,141,331 A | 8/1992 | Oehler et al. | 374/118 |
| 5,178,836 A | 1/1993 | Kitamori et al. | 422/73 |
| 5,254,112 A | 10/1993 | Sinofsky et al. | 606/7 |
| 5,293,873 A | 3/1994 | Fang | |
| 5,348,002 A * | 9/1994 | Caro | 600/310 |
| 5,348,003 A * | 9/1994 | Caro | 600/310 |
| 5,349,954 A * | 9/1994 | Tiemann et al. | 600/342 |
| 5,398,685 A | 3/1995 | Wilk et al. | |
| 5,421,337 A | 6/1995 | Richard-Kortum et al. | |
| 5,465,722 A | 11/1995 | Fort et al. | |
| 5,582,578 A | 12/1996 | Zhong et al. | 601/4 |
| 5,583,634 A | 12/1996 | Andre et al. | 356/318 |
| 5,596,986 A * | 1/1997 | Goldfarb | 600/323 |
| 5,602,894 A | 2/1997 | Bardash | 378/87 |
| 5,615,675 A | 4/1997 | O'Donnell et al. | |
| 5,840,023 A | 11/1998 | Oraevsky et al. | 600/407 |
| 5,977,538 A * | 11/1999 | Unger et al. | 250/227.2 |
| 6,125,290 A * | 9/2000 | Miesel | 600/325 |
| 6,175,759 B1 * | 1/2001 | Chan et al. | 600/431 |

FOREIGN PATENT DOCUMENTS

| | | | | |
|---|---|---|---|---|
| DE | 4400674 A1 | 7/1995 | | G01N/21/31 |
| EP | 0 282 234 A1 | 9/1988 | | A61B/5/00 |
| EP | 919 180 A1 | 6/1999 | | A61B/5/00 |

OTHER PUBLICATIONS

The PCT International Search Report.

* cited by examiner

*Primary Examiner*—Eric F. Winakur
*Assistant Examiner*—Matthew Kremer
(74) *Attorney, Agent, or Firm*—Robert W. Strozier

(57) ABSTRACT

An optoacoustic apparatus is disclosed which includes a radiation source of pulsed radiation and a probe having a front face to be placed in close proximity to or in contact with a tissue site of an animal body. The probe further includes a plurality of optical fibers terminating at the surface of the front face of the probe and connected at their other end to a pulsed laser. The front face of the probe also has mounted therein or thereon a transducer for detecting an acoustic response from blood in the tissue site to the radiation pulses connected to a processing unit which converts the transducer signal into a measure of venous blood oxygenation.

25 Claims, 16 Drawing Sheets

OPTOACOUSTIC MONITORING OF BLOOD OXYGENATION

RELATED APPLICATIONS

This application claims provisional priority to U.S. Provisional Patent Application Ser. No. 60/147,577 filed Aug. 6, 1999.

BACKGROUND OF THE INVENTION

1. Field of the Invention

The present invention relates to an apparatus for non-invasive, real-time, continuous and/or discretely monitoring of cerebral venous oxygenation and a method for continuously and/or discretely monitoring tissue oxygenation including venous oxygenation.

More particularly, the present invention relates to an optoacoustic apparatus including one or more nanosecond pulsed laser, a probe including a sensitive acoustic transducer located in a head of the probe, a fiber-optic delivery system connected to each laser and terminating in the head of the probe, and hardware and software for converting a received acoustic signal into a measure of tissue oxygenation including cerebral venous oxygenation. The present invention also relates to methods for monitoring tissue oxygenation and for making the apparatus of this invention. The present invention is especially well suited for non-invasive monitoring of tissue sites that otherwise would be hard to monitor even with invasive monitoring apparatuses and methods.

2. Description of the Related Art

Clinical Cerebral Oxygenation Monitoring

Over the past fifteen years, compelling clinical evidence has accumulated to suggest that monitoring cerebral oxygenation can detect otherwise unrecognized cerebral ischemia and be used to guide therapeutic interventions. Although randomized clinical trials do not yet demonstrate that interventions based on cerebral oxygenation monitoring can influence outcome, abundant evidence illustrates the association between cerebral hypoxia and worse outcome in such diverse situations as traumatic brain injury and cardiac surgery using cardiopulmonary bypass. In such situations, unlike circumstances in healthy humans, the adequacy of cerebral oxygen delivery (the product of cerebral blood flow and arterial oxygen content) cannot be inferred from measurements of systemic blood pressure and arterial oxygenation because cerebral blood flow is inadequate to satisfy cerebral metabolic demand. To date, the two primary methods used to monitor brain oxygenation are invasive—one requires percutaneous insertion of a catheter into the jugular bulb to continuously measure cerebral venous oxygenation and the other requires insertion of a probe through the skull into the brain parenchyma to measure tissue $PO_2$. Jugular venous bulb monitoring is based on the following equation:

$$CjvO_2 = CaO_2 - CMRO_2/CBF \qquad (1)$$

where $CjvO_2$ represents jugular venous bulb oxygenation content; $CaO_2$ represents arterial oxygen content; $CMRO_2$ represents the cerebral metabolic rate for oxygen; and CBF represents cerebral blood flow [1]. Because oxygen content is linearly related to hemoglobin oxygen saturation at a constant hemoglobin concentration, $SjvO_2$ can be measured or monitored as a surrogate for jugular venous oxygen content.

Jugular venous monitoring provides a global assessment of brain oxygenation, but requires frequent recalibration and is invasive, thereby both introducing the complications of catheter insertion and also delaying the initiation of brain oxygenation monitoring until a patient has been acutely stabilized. Nevertheless, jugular venous bulb measurements have been used in extensive clinical investigations in head-injured patients [2–9] and during cardiac surgery [10–16] and have proven clinically useful in patients who have traumatic brain injury [4, 6] and in patients undergoing cardiopulmonary bypass [10, 17].

Most importantly, single episodes of jugular venous desaturation have been associated with worse outcome after traumatic brain injury [6] and jugular venous desaturation during rewarming after hypothermic cardiopulmonary bypass has been associated with worse cognitive performance after cardiopulmonary bypass [18]. Clinical protocols have been developed that initiate interventions such as changing blood pressure or PaCO2 in response to decreasing $SjvO_2$ [4, 6].

More recently, brain tissue $PO_2$ monitoring has been introduced for the management of patients with traumatic brain injury [19]. In patients with traumatic brain injury, brain tissue $PO_2$ correlates highly with outcome [19]. However, although brain tissue $PO_2$ monitoring provides a precise regional measurement of tissue oxygenation, it provides no information about inadequate tissue oxygenation in remote sites.

Optical Monitoring of Cerebral Blood Oxygenation

Near-infrared spectroscopy, a third, noninvasive method of monitoring cerebral blood oxygenation, utilizes differences in optical absorption coefficients of oxy- and deoxy-hemoglobin [20, 21]. Two wavelengths of the NIR spectral range are usually used in the optical oximeters. One wavelength is shorter and the other is longer than 805 nm (isosbestic point). The technique is promising, but has yet to be satisfactorily calibrated to provide quantitative measurement of cerebral venous oxygenation [22, 23] at least in part because techniques have not been devised to distinguish venous from arterial blood [24].

Moreover, unlike the remarkable success of pulse oximetry for monitoring of systemic arterial hemoglobin saturation, the development of near-infrared monitoring of brain oxygenation has been slowed by the difficulty posed by measuring or estimating the pathlength of scattered light through biologic media [25]. Strong light scattering in tissues presents a great obstacle to quantitative measurement of cerebral blood oxygenation.

Encouraging reports of the use of near-infrared spectroscopy during carotid endarterectomy [26] and cardiac surgery [27] must be balanced against the fact that current technology is qualitative and can be used only as a trend monitor rather than as accurate measurement technique. As a consequence, the technique has yet to be incorporated into routine clinical practice. However, the technology continues to improve as investigators continue to develop more accurate methods of quantifying the signal [28, 29A].

Recently, the method of near-infra-red spectroscopy at two wavelengths coinciding with maxima of oxy and deoxy hemoglobin in microcirculation network of tumors, angiogenesis, was shown useful in differentiating malignant and benign tumors [29B]. However, resolution of pure optical imaging method is insufficient to determine exact dimensions, shape and location of tumors.

Therefore, despite major advances in understanding the physiology of the blood circulation in patients, including patients at high risk for neurologic injury, clinical monitoring of tissue oxygenation including brain oxygenation remains invasive and relatively expensive. Moreover, these procedures generally cannot easily be initiated until a patient is stabilized or until diagnostic tests such as computed tomography or magnetic resonance imaging are completed. Furthermore, these procedures often cannot be initiated until the patient is transferred to the operating suite or intensive care unit. Thus, there is a need in the art for a non-invasive, real-time, continuous and/or discrete monitoring of tissue oxygenation including cerebral venous oxygenation.

SUMMARY OF THE INVENTION

The present invention provides an optoacoustic apparatus including one or more short duration pulsed lasers (preferably the duration is in the nanosecond or shorter duration) and a fiber-optic delivery system including a plurality of optical fibers, where the fibers, at their proximal ends, are optically connected to an output of the laser(s) and terminate in a distal face of an irradiation probe. The apparatus also includes an acoustic probe having a pressure sensing device such as a piezoelectric transducer mounted in a distal face of the acoustic probe. The transducer is connected via a cable which exits from a proximal end of the acoustic probe to a processing unit that converts a transducer output signal into a measure of blood oxygenation of a target tissue. The output signal can include information about venous and/or arterial blood oxygenation depending on the area of irradiation and area of acoustic detection.

The present invention provides an optoacoustic apparatus including one or more short duration pulsed lasers (preferably the duration is in the nanosecond or shorter duration) and a fiber-optic delivery system including a plurality of optical fibers, where the fibers, at their proximal ends, are optically connected to an output of the laser(s). The apparatus also includes a probe having a pressure sensing device such as a piezoelectric transducer mounted in a distal face of a distal end of the probe and a proximal end adapted to receive the fiber-optics delivery system. The optical fibers terminate at or in the distal face of the probe and are preferably distributed around or surround the transducer. The transducer is connected via a cable which exits from the proximal end of the probe to a processing unit that converts the transducer output signal into a measure of blood oxygenation of a target tissue site such as Superior Sagittal Sinus. Again, the output signal can include information about venous and/or arterial blood oxygenation depending on the area of irradiation and area of acoustic detection.

The present invention also provides an optoacoustic apparatus including one or more short duration pulsed lasers and a fiber-optic delivery system including a plurality of optical fibers, where the fibers, at their proximal ends, are optically connected to an output of the laser(s) and to an irradiation probe at its distal end where the fibers terminate in a face of the irradiation probe. The apparatus also includes an acoustic probe having a pressure sensing device such as a piezoelectric transducer mounted in a front face of a distal end of the probe. The transducer is connected via a cable which exits from a proximal end of the acoustic probe to a processing unit that converts the transducer output into a measure of blood oxygenation of a target tissue site such as Superior Sagittal Sinus The present invention also provides an acoustic probe including a housing having a proximal end and a distal end. The probe also includes a distal face in the distal end of the probe, which includes a pressure sensing apparatus such as a piezoelectric transducer mounted thereon or therein and connected to an output cable that exits from the proximal end of the probe, where the distal face is adapted to be placed in close proximity to or in contact with a target tissue site and to receive an acoustic signal therefrom.

The present invention also provides an irradiation probe including a housing having a proximal end and a distal end. The irradiation probe also includes an optical fiber cable including a plurality of optical fibers entering the probe at its proximal end. The fibers terminate at or in a distal face of the distal end of the probe. The optical fibers act as light conduits for laser light energy when connected to a pulsed laser. The irradiation probe is designed to be placed in close proximity to or in contact with a target tissue site to permit pulsed laser light to impinge on the site which is thermalized by tissue in the site resulting in pressure waves or an acoustic signal which are/is detected by the acoustic probe. The detected signal is then related to tissue blood oxygenation—blood oxygen content within the target tissue.

The present invention also provides a probe including a housing having a proximal end and a distal end. The probe also includes a distal face in the distal end of the probe, which includes a pressure sensing apparatus such as a piezoelectric transducer mounted thereon or therein and connected to an output cable that exits from the proximal end of the probe. The probe also includes an optical fiber cable including a plurality of optical fibers entering the probe at its proximal end. The fibers terminate at or in the front face of the probe. The optical fibers act as light conduits for laser light energy when connected to a pulsed laser. The probe is designed to permit pulsed laser light to impinge on a body site which is thermalized by a target tissue site resulting in formation of pressure waves or an acoustic signal which are/is detected by the pressure sensing apparatus. The detected signal is then related to tissue blood oxygenation—blood oxygen content within the target tissue, venous and/or arterial.

The present invention further provides a method for measuring blood oxygenation including the step of directing radiation from a laser via optical fibers terminating in a distal face of a probe of present invention, where the distal face is in optical and acoustic contact with a target tissue site of an animal including a human. The light leaves the probe face and enters the target tissue site causing the production of an acoustic signal in the target tissue site. The acoustic signal is thought to result from thermalization of light energy. The acoustic signal is received by a pressure sensing apparatus such as a transducer mounted on or in the distal or front face of the probe producing a output signal. The signal is then transmitted to a processing unit which converts the signal into a measure of blood oxygenation. The method can also include displaying the measurement on a display device. Preferably, the radiation is pulsed and particularly, the radiation is pulsed in a nanosecond time frame.

The present invention also provides a method for monitoring blood oxygenation in a tissue or a blood vessel including irradiating the tissue or the blood vessel with at least one laser pulse. The pulse causes the generation of an acoustic signal corresponding to a distribution of thermoelastic optoacoustic pressure profiles of the absorbed laser energy in the tissue or vessel. The signal is detected with at least one acoustic detector in a time-resolved manner. The detector signal is then analyzing and the temporal profiles and/or signal amplitudes of the optoacoustic waves with a related to the oxygenation level of hemoglobin in blood within the tissue or vessel. The method can include laser light at a or single wavelength or multiple wavelengths depending on properties or factors such as the location of the tissue or vessel, the amount of other body structures to be penetrated (bone, thick tissue, etc.), blood concentration in the tissue or vessel or other properties or factors.

The present invention also provides a system for carrying out the above-states method including a pulsed laser system or other system capable of generating short optical pulses to provide irradiation of a tissue or vessel. The systems also includes a light communication system such as a fiber-optic system or articulated mirror arm optical system for delivering laser pulses to the tissue or vessel and an acoustic detection systems including at least one acoustic transducer for pressure profile detection with sufficient sensitivity, temporal resolution, and bandwidth so that thermoelastic optoacoustic pressure profiles of the absorbed laser energy in the tissue or vessel can be detected. The system also includes an adjustable holder for the light delivery system and the acoustic transducer(s) to provide appropriate irradiation conditions and acoustic contact between the investigated tissue or vessel and the acoustic transducer(s) and an electronic system for signal recording and processing. The system can also include a digital processing or computer system that converts a signal from the acoustic detection system into a measure of blood oxygenation in the tissue or vessel.

The present invention still further provides a method for relating an acoustic signal to an oxygenation index for blood in a target tissue site of an animal, including a human.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
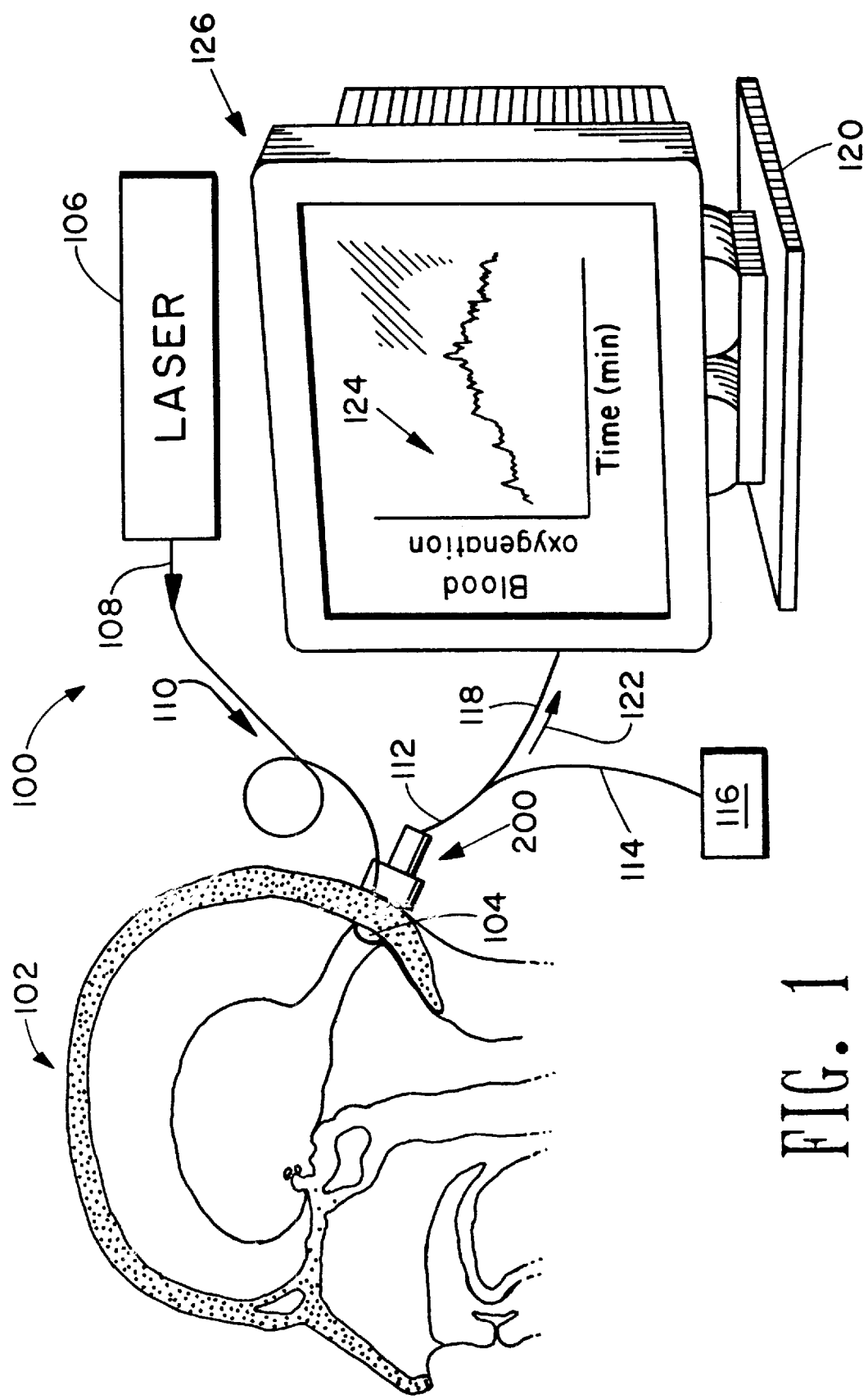
FIG. 1 depicts a schematic view of another preferred embodiment of an optoacoustic blood oxygenation apparatus of the present invention in operation for monitoring cerebral blood oxygenation of the Superior Sagittal Sinus.

The inventors have found that a new, cost effective, efficient, non-invasive optoacoustic apparatus and system can be constructed for monitoring the oxygenation of blood in a target site of an aminal body including a human body. The inventors have also found that a method using the optoacoustic monitoring apparatus can be implemented under manual or automatic (computer) control for supervision on a continuous or discrete basis blood oxygenation of blood within a given tissue site such as the oxygenation of cerebral venous blood.

The inventors have also found that a novel optoacoustic technique for monitoring of cerebral venous oxygenation can be constructed. This technique will allow non-invasive, real-time, accurate, and continuous measurements of cerebral venous oxygenation. Low cost and portability of the optoacoustic system will permit wide application in the field (as in military or mass-casualty settings), in emergency care vehicles, and in hospitals. Due to the submillimeter spatial resolution of the optoacoustic technique, the system can also be used for regional monitoring of venous oxygenation in different areas of the brain. The system can also be used to monitor blood oxygenation in other tissue sites and organs.

The present invention can be used for non-invasive monitoring of blood oxygenation in tissues or directly in blood vessels. Accurate and continuous monitoring of blood oxygenation in the brain, heart, liver or other organs offers great promise in the management and diagnosis of many diseases. The optoacoustic monitor can be used for measurement of blood oxygenation in the pulmonary artery and cardiac ventricles in patients with heart disease or circulatory shock. Monitoring cerebral blood oxygenation is vital for the management of life-threatening illnesses, including severe traumatic brain injury. The apparatus of the present invention should find broad application in several large patient populations, including patients with heart diseases, patients with circulatory shock, patients with traumatic brain injury, patients undergoing cardiac surgery, patients with a variety of acute neurological insults such as aneurisms and stokes. Other applications include blood oxygenation monitoring of patients during acute or chronic conditions in the liver, kidneys or other organs or large blood vessels.

The present invention can be performed in two detection modes: forward mode and backward mode. Forward mode permits laser irradiation and pressure wave detection to occur at different sides or surfaces of a tissue site or organ, preferably, where the sides are opposed. In the backward mode, laser irradiation and pressure wave detection occur from the same surface of tissue. When the apparatus of this invention is used to monitor blood oxygenation of large organs or large tissue sites such as the brain, the apparatus is preferably operated in the backward mode. While, when monitoring blood oxygenation of small organs or small tissue sites, the apparatus can be used in either mode with the forward mode being preferred.

The inventors have found that laser optoacoustics, recently proposed as a technique for tissue characterization and diagnostic imaging [30–33], can help overcome problems associated with pure optical techniques, which suffer from loss of diagnostic information due to strong light scattering by tissue. Optoacoustics utilizes sensitive detection of laser-induced ultrasonic waves (an acoustic signal) instead of the detection of scattered photons. An advantage of acoustic wave detection compared with the detection of light is that the propagation of acoustic waves in tissues is much less susceptible to scattering.

The laser light can be of any desired wavelength or combination of wavelengths provided that the wavelength of the light is capable of giving rise to an acoustic response that can be related to a measure of blood oxygenation in the tissue or vessel. Generally, the light wavelength is between about 600 and about 1400 nm and preferably between about 800 nm and 1200 nm. For those systems of the present invention that use two or more lasers, each laser should have a wavelength in the general or preferred range. However, other light sources can be used provided that the light is sufficiently filtered to have a narrow bandwidth with in the general or preferred wavelength range.

The apparatus of the present invention can be used to irradiation one or more tissue sites and to detect induced acoustic responses from one or more tissue sites or blood vessels. The tissue and/or blood vessels can be internal or external and the irradiation and/or acoustic detection can be on an outer surface of a body or endoscopically position in the interior of a body. Thus, the irradiation probe and/or the acoustic detection probe can be associated with an endoscope or other instrument inserted inside a body or body cavity.

The apparatus of the present invention can be used to monitor blood oxygenation in veins and/or arteries generally in the body or in a specific organ or tissue. The apparatus can be used to monitor blood oxygenation (arterial or venous) in brain tissue, including the Superior Sagittal Sinus (SSS) and other intracerebral vessels, in neck vessels including the jugular bulb, in the liver, in portal veins, in pulmonary arteries or veins, in the kidneys, etc. The apparatus of the present invention can also be used intra-operatively (during an operating procedure) on exposed brain tissue, SSS, myocardium or other tissues or vessels. The apparatus of this invention can also be used in conjunction with absorbing dyes that increase the accuracy of blood oxygenation measurement using optoacoustics.

The present invention can also be used as a diagnostic technique for differentiating tumors based on their blood oxygenation, because malignant tumors have different blood oxygenation than benign tumors.

Time-resolved detection of the pressure profiles by ultrasound transducers and analysis of the pressure signals allow reconstruction of optoacoustic images which resemble distribution of optical absorption in the irradiated tissue. In contrast to pure optical methods, in which diagnostic information about tissue structure is integrated over the entire optical path, the laser optoacoustic imaging permits direct reconstruction of the absorbed energy distribution from the profile of laser-induced pressure [30–36]. The time-resolved detection and analysis of the laser-induced ultrasonic waves allows visualization of tissue structure at depths as great as eight centimeters with spatial resolution exceeding 0.5 millimeters in optically turbid and opaque tissues [36–38], reconstruction optoacoustic images [39, 40] and non-invasive determination of properties such as blood oxygenation in a target tissue. The inventor have found that laser optoacoustic imaging of blood combines the merits of optical tomography (high optical contrast) and ultrasound imaging (insignificant scattering of acoustic waves) to yield a noninvasive diagnostic modality for monitoring of blood oxygenation with high contrast, sensitivity and resolution. For additional information on the use of optoacoustic imaging in tissues, reference is made to U.S. Pat. No. 5,840,023 issued Nov. 4, 1998 [41] and U.S. patent application Ser. No. 09/412,852 filed Oct. 21, 1999 [42], incorporated herein by reference.

The present invention provides the capability of obtaining absolute blood oxygenation measurements with high sensitivity. This invention utilizes the optoacoustic effect which is based on generation of pressure waves in tissue due to absorption of pulsed optical radiation, preferably, laser radiation. The inventors have found that the amplitude and profile of the induced acoustic/pressure waves depend linearly on hemoglobin saturation; that laser-induced ultrasonic or acoustic waves propagate through the skull and skin with insignificant scattering; and that the waves deliver diagnostic information to the acoustic transducer without distortion.

The present invention provides the capability of continuous, real-time monitoring or periodic monitoring of blood oxygenation in a target body site. Data acquisition and processing can be performed at any given time interval such as once a second, thereby providing nearly instantaneous warning of a potentially hazardous change in the balance between cerebral blood flow and cerebral oxygen utilization.

The present invention provides the capability to directly measure cerebral blood oxygenation with high spatial resolution. Previous studies demonstrated that spatial z-axial (in depth) resolution of the optoacoustic technique is better than 0.5 mm [36–38].

The present invention provides a low cost and compact diagnostic apparatus, which is minimally invasive or completely non-invasive. The amount of laser energy applied for optoacoustic monitoring is small and does not induce thermal or mechanical damage to tissues. The apparatus and methods of this invention are versatile and can be used with or without modification, usually minimal, for monitoring of blood oxygenation in brain and other organs and tissue sites. The organs or tissues sites include, without limitation, a heart tissue, a pulmonary artery or an aorta, an artery or vein in the neck or brain, and the blood oxygenation is used to detect or monitoring stroke, a brain tissue, a superior sagittal sinus, an intracerebral vessel, a jugular bulb, a liver tissue, a portal vein, a kidney tissue, a kidney vein or artery or any other tissue or vessel.

The signal process apparatus of the present invention can comprise any analog or digital processing unit or computer capable of converting a signal into an output. Such devices include, without limitation, any digital processing unit comprising a processing unit, memory, peripherals, an operating systems and communication hardware and software. Illustrative examples include personal computers, mini-mainframe computers, or the like.

Figure 17:
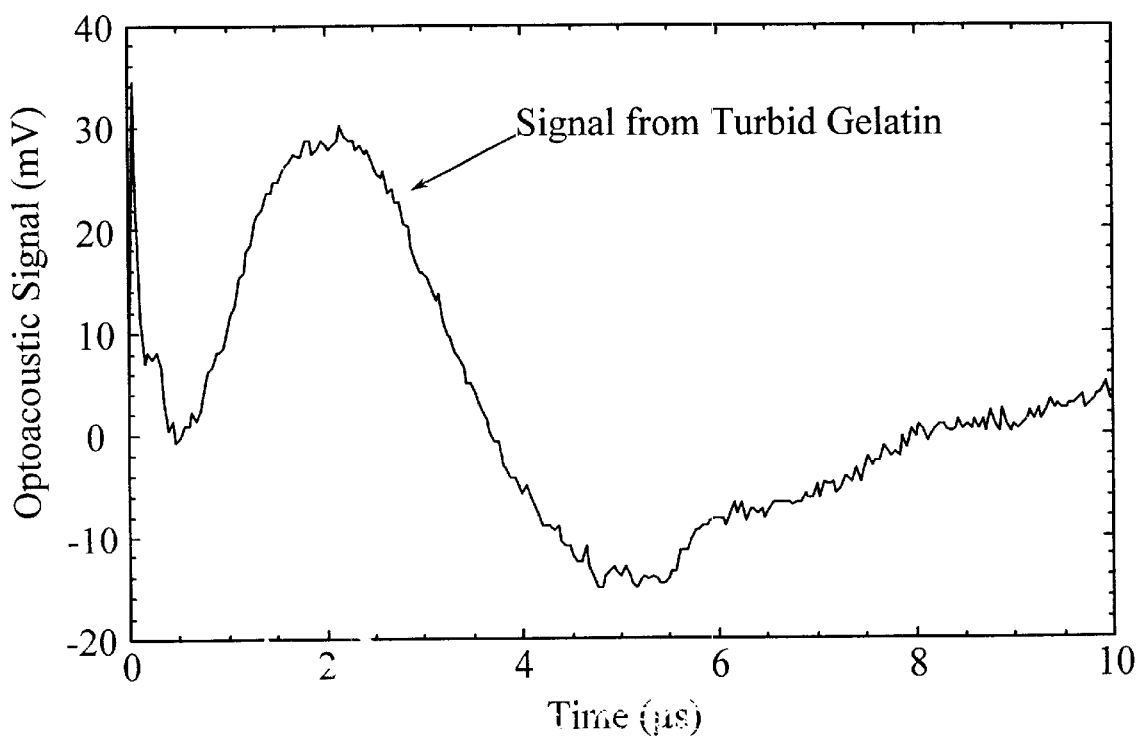
FIG. 17 graphs an acoustic signal recorded with an optoacoustic probe from 15-mm turbid uniform gelatin simulating thick tissue.
Figure 18:
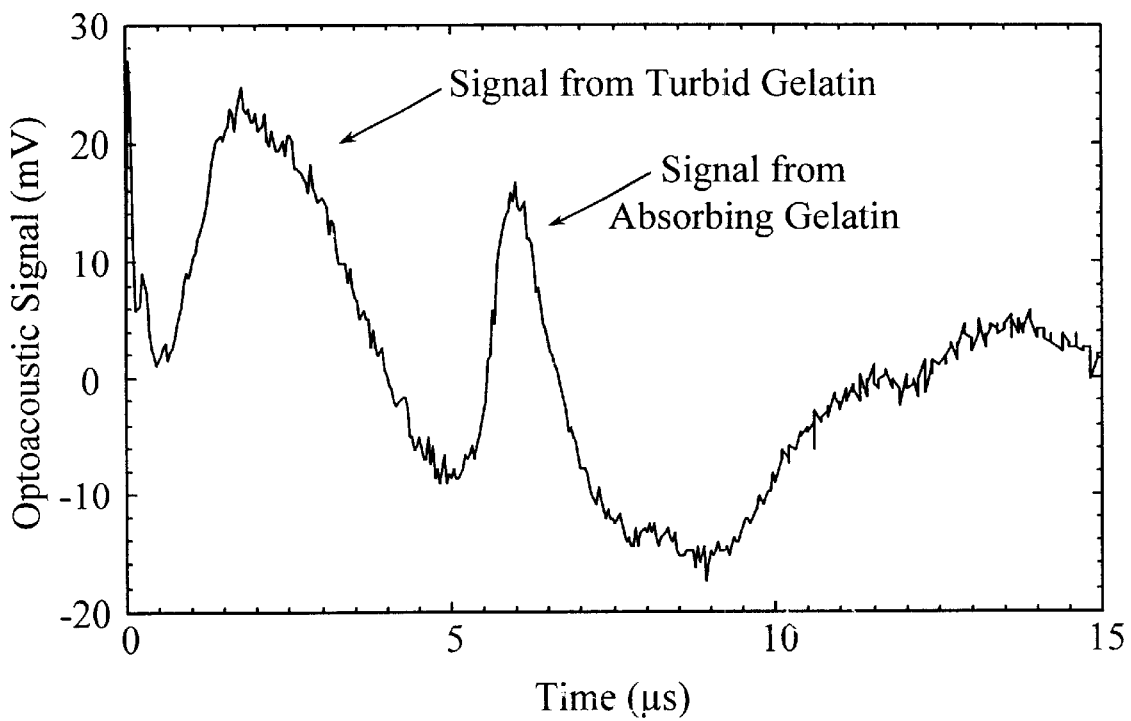
FIG. 18 graphs an acoustic signal recorded with the optoacoustic probe from a layered tissue phantom (9-mm turbid gelatin slab and a slab of absorbing gelatin simulating blood under thick tissue)
Figure 19:
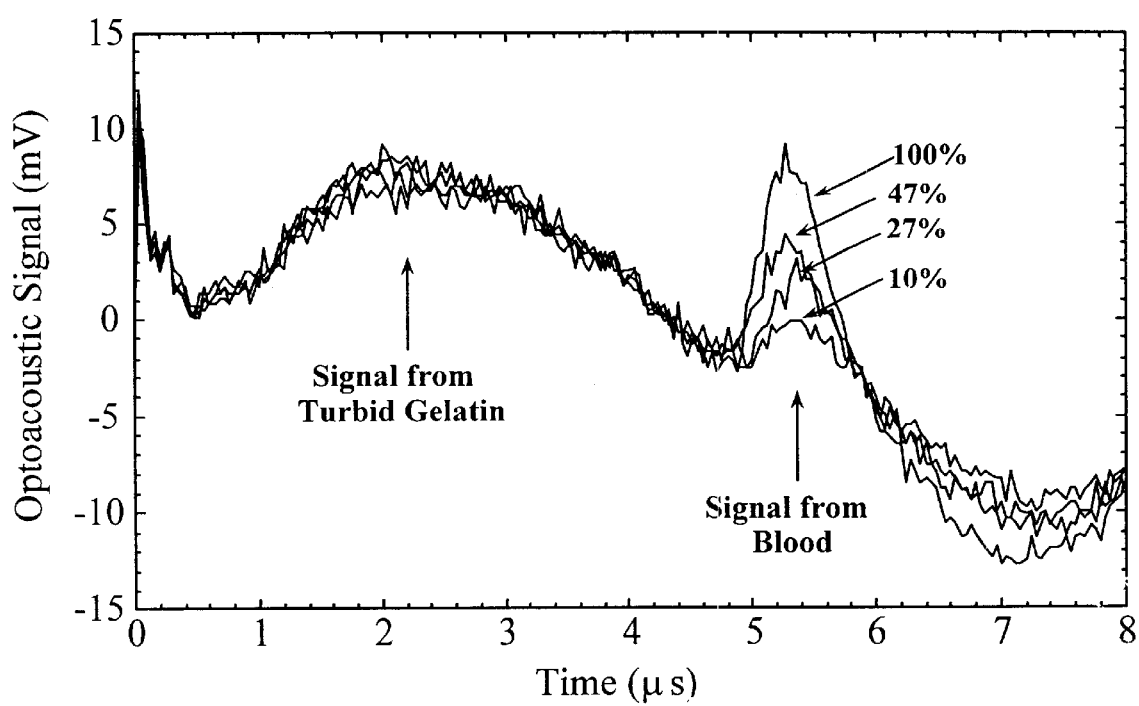
FIG. 19 graphs acoustic signals recorded with the optoacoustic probe from a turbid tissue phantom with blood at different oxygenation (100%, 47%, 27%, and 10%) circulating in a 5-mm tube simulating a blood vessel.

In preliminary studies, the inventors found that when operated in the forward mode, an apparatus of the present invention verified the following: (1) linear dependence of the amplitude and slope of optoacoustic pressure waves on blood hemoglobin saturation as measured with a CO-Oximeter; (2) detection of optoacoustic signals through bone of a thickness comparable to human skull above the Superior Sagittal Sinus (SSS); (3) continuous, real-time measurement during rapid changes in blood oxygenation induced by insufflation with air; (4) the ability of optoacoustic technique to detect small (2–6 mm in diameter) volumes with increased optical absorption deeply located (up to 60 mm) in a medium with lower absorption, i.e., a simulation of blood in vessels surrounded by tissues with low blood content (skull, skin, etc.) [36–38]; (5) high axial resolution (0.5 mm) [36–38]; (6) a probe for backward mode acoustic detection was constructed with optical fibers surrounding a transducer as illustrated in FIG. 1; (7) testing of the backward mode probe assembly for detection of blood oxygenation through simulated tissue as shown in FIGS. 17 & 18; and (8) using the backward mode probe assembly for real-time, continuous monitoring of blood oxygenation in vitro as shown in FIG. 19.

Theoretical Background

The generation of acoustic waves by the consecutive transformation of light energy into heat and then into mechanical stress is referred to as the thermo-optical mechanism of pressure generation [44]. The absorption of laser radiation in a medium followed by a fast non-radiative relaxation of the excited states converts laser energy into heat. Subsequently, thermal expansion of a uniform medium instantaneously heated by a short laser pulse with the incident laser fluence, $F_0$, induces an instant pressure rise, $P(z)$, in the irradiated volume upon stress-confined irradiation conditions [44]:

$$P(z)=(\beta c_s^2/C_p)\mu_a F=\Gamma\mu_a F(z)=\Gamma\mu_a F_0 e^{-\mu_a z} \quad (2)$$

where $\beta[1/^\circ C.]$ is the thermal expansion coefficient; c is the speed of sound; $C_p[J/g^\circ C.]$ is the heat capacity at constant pressure; $F(z)[J/cm^2]$ is the laser fluence; and $\mu_a [cm^{-1}]$ is the absorption coefficient of the medium. The pressure increases with the absorbed energy density, $E_{abs}[J/cm^3]$, which in turn equals the product of the absorption coefficient and fluence. Pressure in (2) can be expressed in $J/cm^3$ or in bar (1 $J/cm^3$=10 bar). The expression $(\beta c_s^2/Cp)$ in equation (2) represents the Gruneisen parameter, $\Gamma$ (dimensionless). The factor $\exp(-\mu_a z)$ represents exponential attenuation of the optical radiation in the medium.

According to equation (2), optoacoustic pressure is proportional to the Gruneisen parameter, fluence, and absorption coefficient of the medium. Equation (2) is valid for blood in the visible and near-infrared spectral range because the absorption coefficient of blood is greater than or close to the reduced scattering coefficient, $\mu's=\mu_s(1-g)$, where $\mu_s$ is the scattering coefficient and g is the anisotropy factor [21]. It is well established that the absorption coefficient of blood in the visible and near-infrared spectral range is dependent on hemoglobin saturation (i.e., oxygenation). This principle is utilized in conventional optical oximeters. Therefore, both the amplitude and slope of the generated optoacoustic pressure induced in blood depends on oxygenated hemoglobin concentration of the blood.

Since z and t are related by the simple equation:

$$z=c_s t \quad (3)$$

the spatial distribution of laser-induced pressure $P(z)$ is detected by an acoustic transducer as a temporal profile $P(t)$:

$$P(t)=\Gamma\mu_a F_0 e^{-\mu_a c_s t} \quad (4)$$

Therefore, by recording and analyzing the temporal profile of optoacoustic pressure signal induced in blood, one can measure the absolute value of blood oxygenation with high accuracy.

The high z-axial resolution of the optoacoustic technique permits direct measurement of blood oxygenation target tissue sites such as in the SSS, because the signal from the blood arrives at the acoustic transducer at a time defined by equation (3).

Tissues are strongly scattering media. Three major optical parameters are responsible for distribution of light in tissues: absorption, scattering, and effective attenuation, $\mu_{eff}$, coefficients. The effective attenuation coefficient is related to $\mu_a$ and $\mu_s$:

$$\mu_{eff}=(3\mu_a(\mu_a+\mu_s(1-g)))^{1/2} \quad (5)$$

and characterizes penetration of light in tissue [21]. Light penetration depth is defined as $1/\mu_{eff}$. Absorption and reduced scattering coefficients of tissues are low in the near-infrared spectral range (from 600 to 1300 nm) that results in deeper penetration of near-infrared radiation compared with that of other parts of the spectrum. Application of near-infrared radiation will allow sufficient penetration of light for optoacoustic monitoring of blood oxygenation. Laser irradiation and optoacoustic waves will not generate any damage to brain because temperature (0.1° C.) and pressure (0.2 bar) rise are below the safe levels [45–48].

Design of the Laser Optoacoustic Monitoring System in Backward Mode

Referring now to FIG. 1, a non-invasive, continuous optoacoustic system for monitoring cerebral blood oxygenation 100 is shown to include a probe 200 positioned against a human head 102 adjacent the Superior Sagittal Sinus 104. The system 100 also includes a laser 106 having an output 108 in optical communication with the probe 200 via an optical fiber cable 110. The system 100 also includes an electrical cable 112, which includes a power supply cable 114 to supply power to the probe 200 from a power supply 116 and an output signal cable 118 in electrical communication with a computer 120, where the computer 120 converts an output signal 122 from the probe 200 into a graphical measure of blood oxygenation 124 as shown displayed on a computer screen 126.

The system 100 was assembled using the following components: a compact nanosecond Nd:YAG laser, a novel optoacoustic probe, and a computer (PC) for data acquisition and signal processing. The probe is designed to be held in close proximity to or in contact with the skin surface above the SSS when used to measure cerebral blood oxygenation and to detect acoustic waves induced in blood circulating in it. The components were designed to be assembled on a cart for ease of transport and use. Generally, the pulsed have a relatively short duration. Preferably, the short duration is less than about 100 ns (nanoseconds), more preferably, less than about 50 ns, particularly, less than about 25 ns and especially, less than or equal to about 10 ns.

The preferred laser is a Q-switched Nd:YAG laser ($\lambda=1064$ nm) with ultrastable pulse energy such as Q-switched Nd:YAG Model: Ultra CFR, manufactured Big Sky Technologies Inc., MO. This compact laser with pulse energy of up to about 55 mJ and stability of about 0.3% is most suitable for our system. However, other similar lasers can be used as well. The dimensions of the laser head (2 lbs) and power supply (30 lbs) are 3×2×6.67 inch and 8×14×14 inch. The laser does not need external water cooling. In applications were blood oxygenation monitoring through dense tissue and/or thick such as bone or thick soft tissue is required, then a higher energy laser system may be necessary such as higher power lasers available from several manufacturers including Big Sky Technologies Inc.

Referring now to FIGS. 2A–F, the probe 200 includes a housing 202 having a distal face 204 designed to be held in close proximity to or in contact with a body, tissue or organ site associated with a target site for which blood oxygenation data is sought. The distal face 204 includes a plurality of tubes 206 into which optical fibers 208 are inserted so that ends 210 of the optical fibers 208 are essentially flush with the face 204. The face 204 also includes a transducer 212 mounted therein so that an outer surface of the transducer 212 is also essentially flush with the face 204. The optical fibers 208 are bundled together into the optical fiber cable 110 which exits from a proximal end 214 and is connected to the laser output 108. The transducer 212 is connected to the electrical cable 114, which also exits the probe 200 from its proximal end 214. The optical fiber ends 210 surround the transducer 212.

Figure 2:
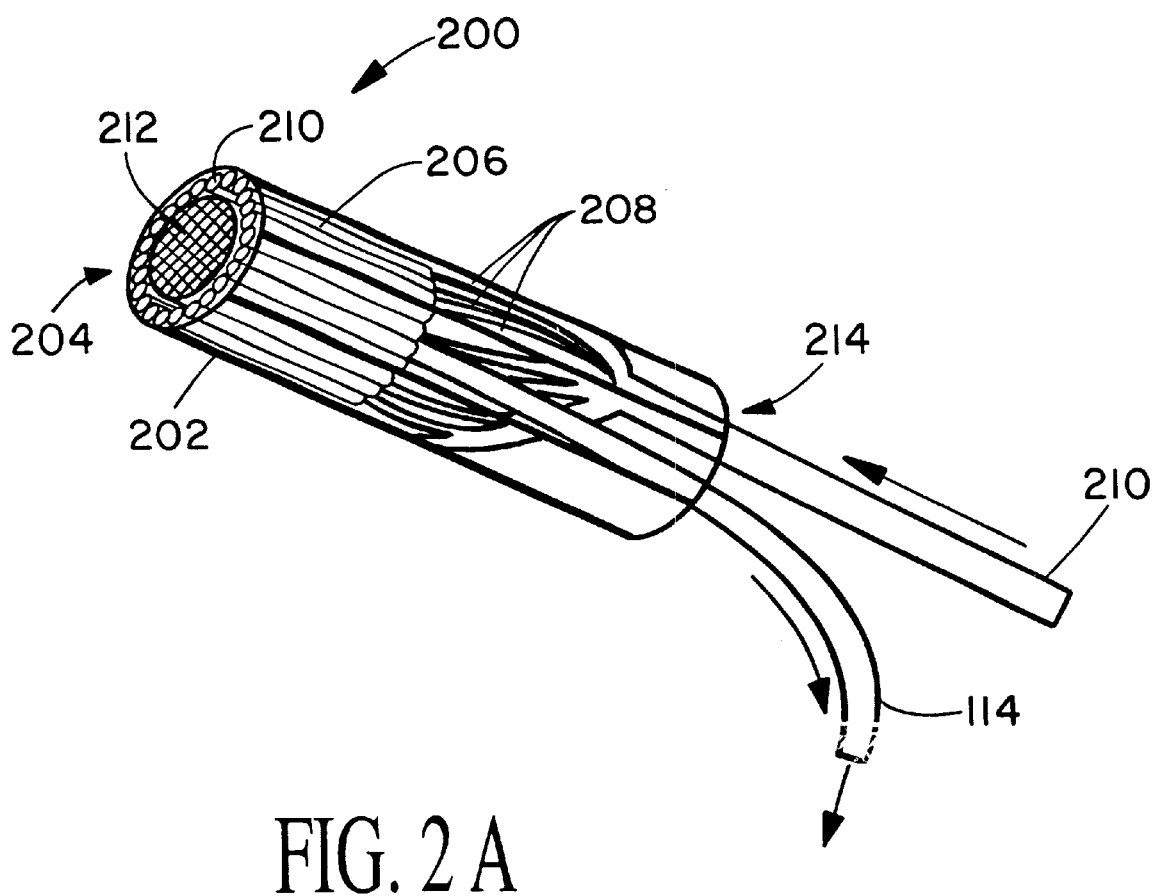
FIG. 2A depicts a perspective view of a preferred embodiment of a probe of the present invention using a single laser.
FIG. 2B depicts a lateral cross-sectional view of the probe of FIG. 2A.
FIG. 2C depicts an end view of a face profile of the probe of FIG. 2A.
FIG. 2D depicts an end view of another face profile of the probe of FIG. 2A.
FIG. 2E depicts an end view of another face profile of the probe of FIG. 2A.
FIG. 2F depicts an end view of another face profile of the probe of FIG. 2A.
Figure 2B:
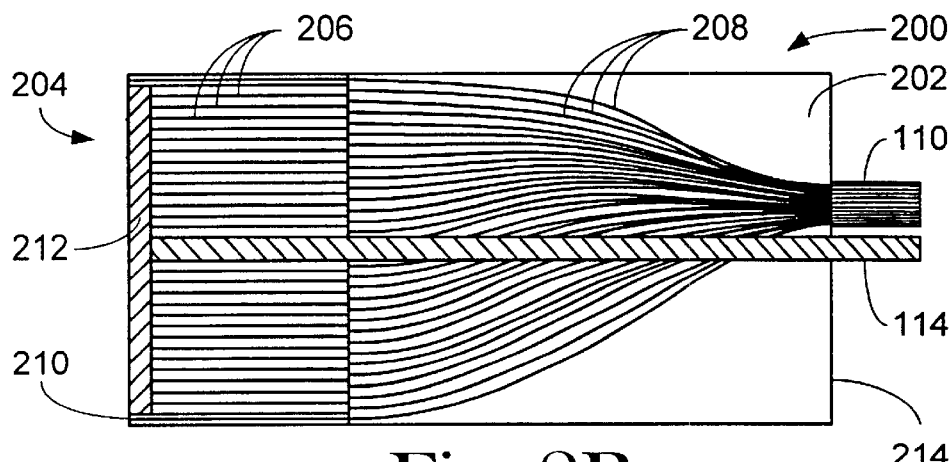
Figure 2C:
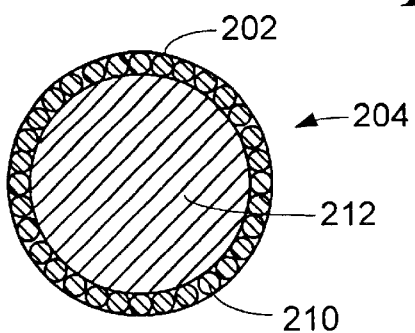
Figure 2D:
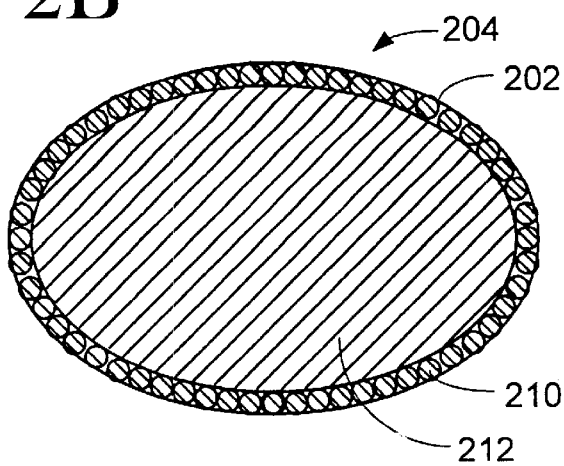
Figure 2E:
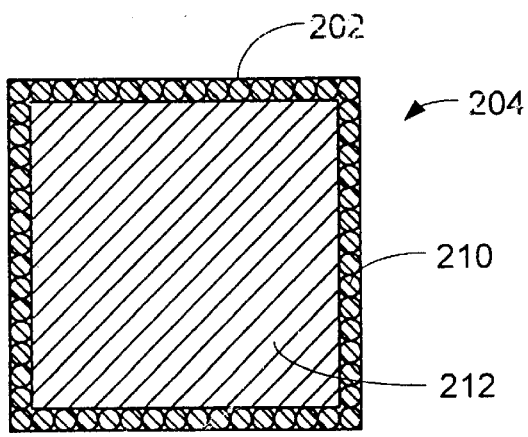
Figure 2F:
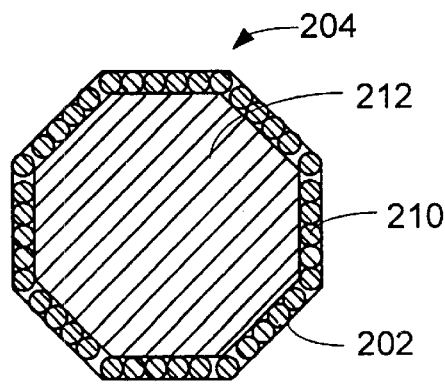

The distal face 204 of the probe 200 can be of any desired shape (regular or irregular) with the optical fiber ends 210 surrounding the transducer 212. Several illustrative examples of such probe designs are described below and shown in FIGS. 2C–F. Referring now to FIG. 2C, the face 204 is circular with a circular transducer 212 and the tubes 206 containing the fiber ends 210 surrounding the circular transducer 212. The housing 202 also has a circular cross-section and the probe 200 is cylindrically shaped. Referring now FIG. 2D, the face 204 is oval with an oval shaped transducer 212 and the tubes 206 containing the fiber ends 210 surrounding the oval shaped transducer 212. The housing 202 also has an oval cross-section and the probe 200 is squashed cylindrical shape. Referring now FIG. 2E, the face 204 is square (any quadrilateral) with a square (any quadrilateral) transducer 212 and the tubes 206 containing the fiber ends 210 surrounding the square transducer 212. The housing 202 also has a square (any quadrilateral) cross-section and the probe 200 is a rectangular solid. Referring now FIG. 2F, the face 204 is octagonal (any polygon) with an octagonal (any polygon) transducer 212 and the tubes 206 containing the fiber ends 210 surrounding the octagonal transducer 212. The housing 202 also has an octagonal (any polygonal) cross-section and the probe 200 is octagonal solid. Of course, the probe 200 can include any shaped face and housing and any shaped transducer provided that the optical fibers surround the transducers. It should also be recognized that the optical fiber ends do not have to completely surround the transducer. Moreover, multiple transducers can be used as well.

Referring now to FIGS. 3A–F, the probe 300 includes a housing 302 having a distal face 304 designed to be held in close proximity to or in contact with a body, tissue or organ site associated with a target site for which blood oxygenation data is sought. The distal face 304 includes a plurality of tubes 306 into which two sets of optical fibers 308 and 309 are inserted so that ends 310 and 311 of the optical fibers 308 and 309 are essentially flush with the face 304. The face 304 also includes a transducer 312 mounted therein so that an outer surface of the transducer 312 is also essentially flush with the face 304. The optical fibers 308 are bundled together into a first optical fiber cable 110 and second optical fiber cable 111 which exit from a proximal end 314. The first optical cable 110 is connected to the laser output 108, while the second optical cable 111 is connected to a second laser output (not shown). The second laser has a wavelength different from the first laser, preferably a lower wavelength, such a short duration pulsed, Alexandrite laser ($\lambda=750$ nm). Two laser are sometimes advantages because you can irradiation the target tissue at a wavelength above and below the isobestic point. The transducer 312 is connected to the electrical cable 114, which also exits the probe 300 from its proximal end 314. In distinction to the probe of FIGS. 2A–F, the probe 300 includes optical fibers 308 and 309 from two different lasers. Using two different pulsed laser sources increases the information retrievable from the transducer output signal because the different wavelength of the excitation laser pulses tends to cause different tissue features such as blood to respond differently. In the case of blood, the two lasers can work to improve accuracy of blood oxygenation measure. Again, the optical fiber ends 310 and 311 surround the transducer 212.

Figure 3A:
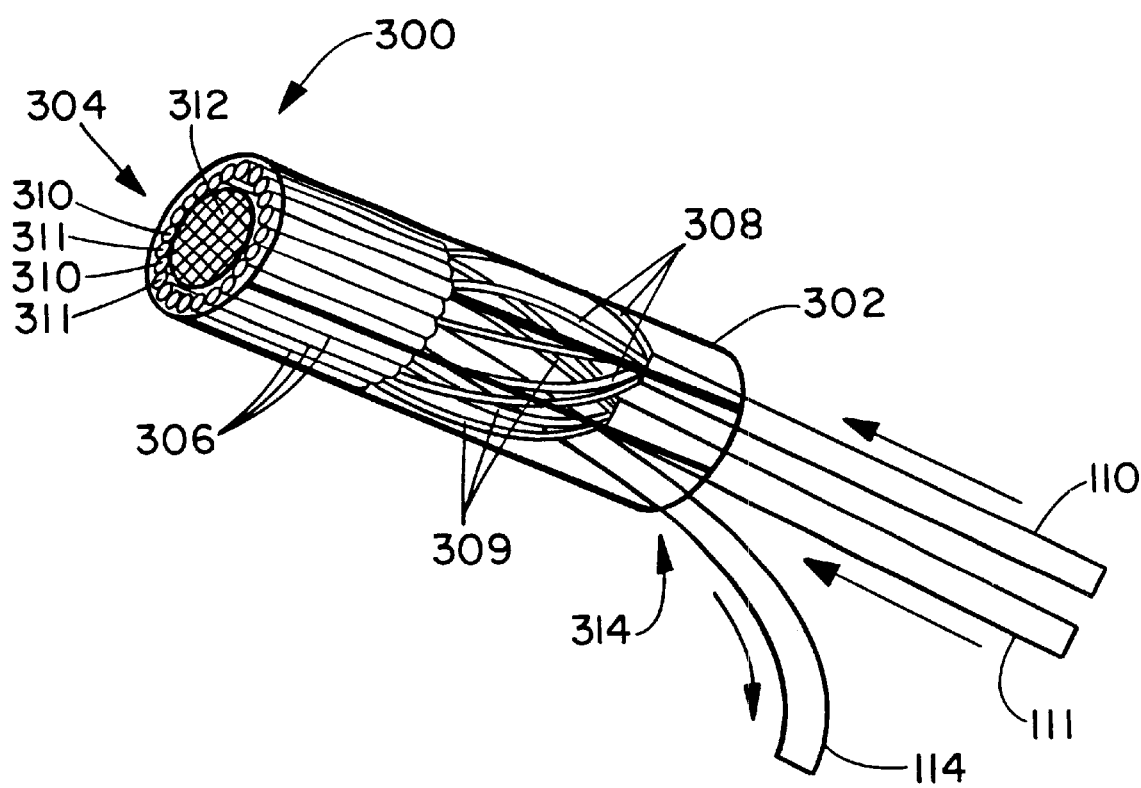
FIG. 3A depicts a perspective view of another preferred embodiment of a probe of the present invention using two lasers.
Figure 3B:
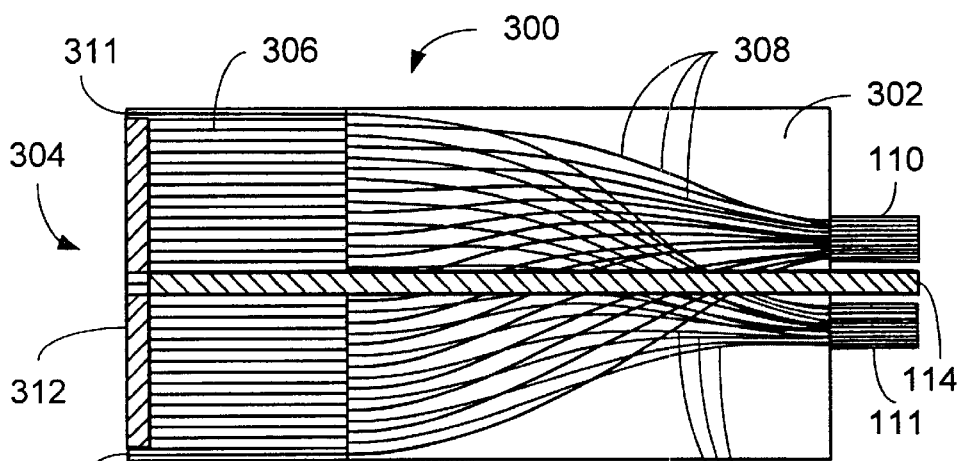
FIG. 3B depicts a cross-sectional view of the probe of FIG. 3A.
Figure 3C:
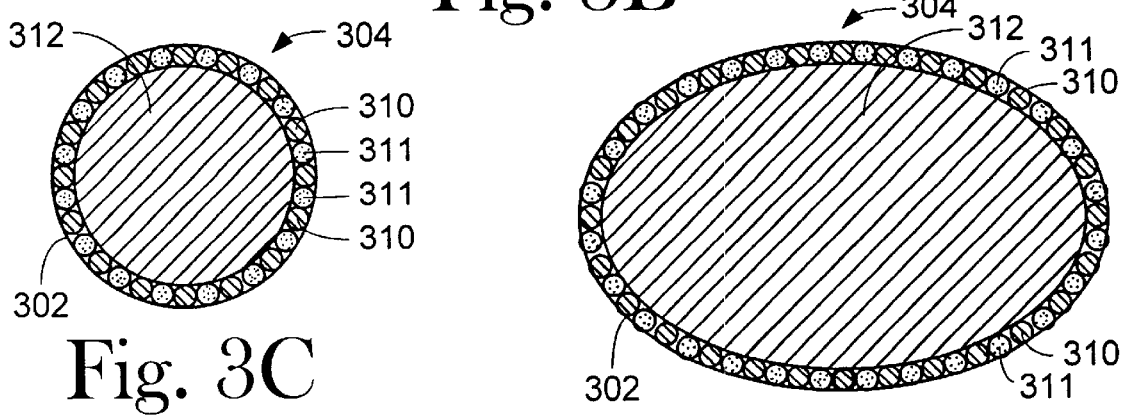
FIG. 3C depicts an end view of a face profile of the probe of FIG. 3A.
Figure 3D:
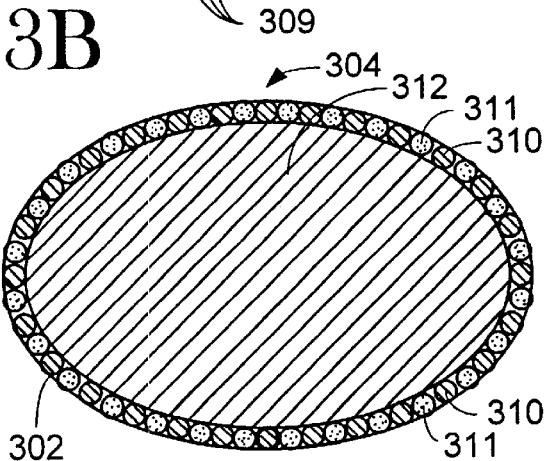
FIG. 3D depicts an end view of another face profile of the probe of FIG. 3A.
Figure 3E:
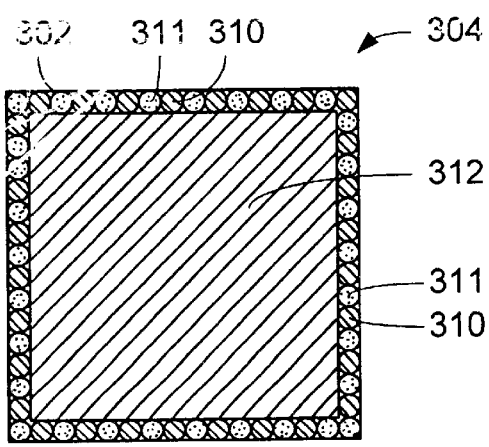
FIG. 3E depicts an end view of another face profile of the probe of FIG. 3A.
Figure 3F:
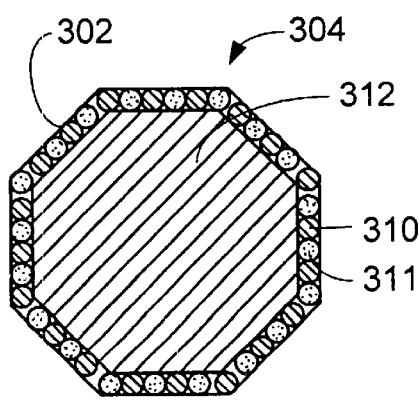
FIG. 3F depicts an end view of another face profile of the probe of FIG. 3A.

As in the probes of FIGS. 2A–F, the distal face 304 of the probe 300 can be of any desired shape with the optical fiber ends 310 surrounding the transducer 312. Several illustrative examples of such probe designs are described below and shown in FIGS. 3C–F. Referring now to FIG. 3C, the face 304 is circular with a circular transducer 312 and the tubes 306 containing the fiber ends 310 surrounding the circular transducer 312. The housing 302 also has a circular cross-section and the probe 300 is a cylinder. Referring now FIG. 3D, the face 304 is oval with an oval transducer 312 and the tubes 306 containing the fiber ends 310 surrounding the oval transducer 312. The housing 302 also has an oval cross-section and the probe 300 is a squashed cylinder. Referring now FIG. 3E, the face 304 is square (any quadrilateral) with a square (any quadrilateral) transducer 312 and the tubes 306 containing the fiber ends 310 surrounding the square transducer 312. The housing 302 also has a square (any quadrilateral) cross-section and the probe 300 is a quadrilateral solid. Referring now FIG. 3F, the face 304 is octagon (any polygon) with an octagon (any polygon) transducer 312 and the tubes 306 containing the fiber ends 310 surrounding the octagonal transducer 312. The housing 302 also has an octagon (any polygon) cross-section and the probe 300 is octagonal (any polygonal) solid.

Referring now to FIGS. 4A–E, the probe 400 includes a housing 402 having a distal face 404 designed to be held in close proximity to or in contact with a body, tissue or organ site associated with a target site for which blood oxygenation data is sought. The distal face 404 includes a plurality of tubes 406 into which optical fibers 408 are inserted so that ends 410 of the optical fibers 408 are essentially flush with the face 404. The face 404 also includes a transducer 412 mounted therein so that an outer surface of the transducer 412 is also essentially flush with the face 404. The optical fibers 408 are bundled together into the optical fiber cable 110 which exits from a proximal end 414 and is connected to the laser output 108. The transducer 412 is connected to the electrical cable 114, which also exits the probe 400 from its proximal end 414. The optical fiber ends 410 surround the transducer 412.

Figure 4A:
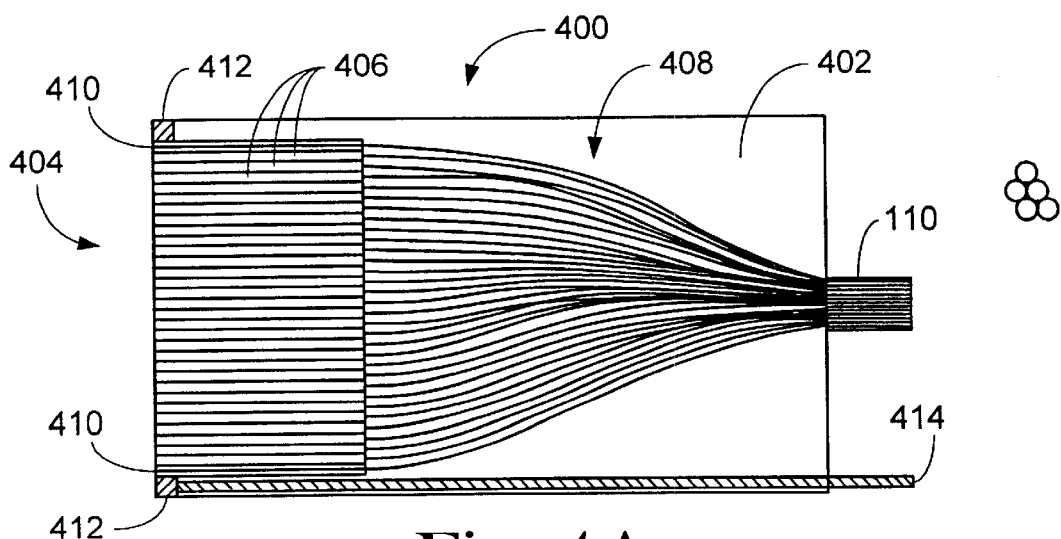
FIG. 4A depicts a cross-sectional view of another preferred embodiment of a probe of the present invention.
Figure 4B:
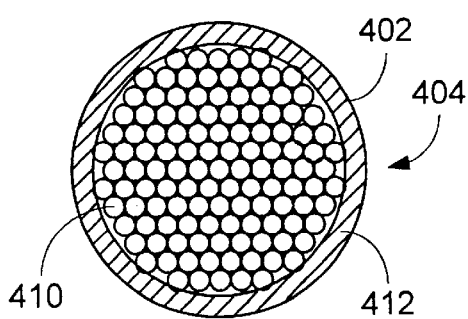
FIG. 4B depicts an end view of a face profile of the probe of FIG. 4A.
Figure 4C:
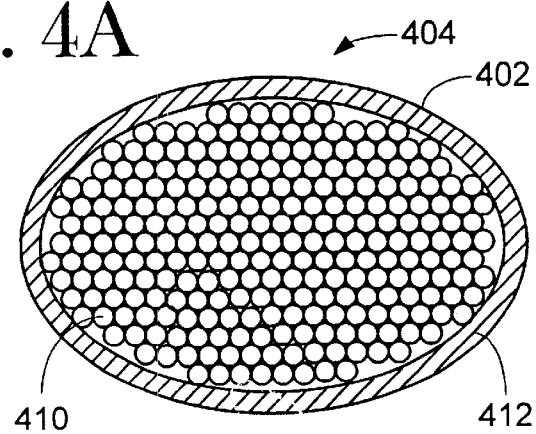
FIGS. 4C, 4D and 4E depict an end view of another face profile of the probe of FIG. 4A.
Figure 4D:
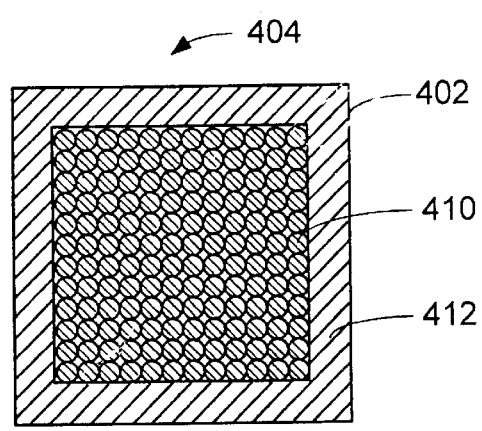
Figure 4E:
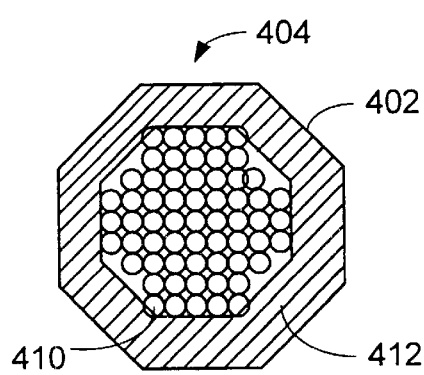

The distal face 404 of the probe 400 can be of any desired shape with the transducer 412 surrounding the optical fiber ends 410. Several illustrative examples of such probe designs are described below and shown in FIGS. 4B–E. Referring now to FIG. 4B, the face 404 is circular with a circular transducer 412 and the tubes 406 containing the fiber ends 410 surrounded by the circular transducer 412. The housing 402 also has a circular cross-section and the probe 400 is cylindrically shaped. Referring now FIG. 4C, the face 404 is oval with an oval shaped transducer 412 and the tubes 406 containing the fiber ends 410 surrounded by the oval shaped transducer 412. The housing 402 also has an oval cross-section and the probe 400 is squashed cylindrical shape. Referring now FIG. 4D, the face 404 is square (any quadrilateral) with a square (any quadrilateral) transducer 412 and the tubes 406 containing the fiber ends 410 surrounded by the square transducer 412. The housing 402 also has a square (any quadrilateral) cross-section and the probe 400 is a rectangular solid. Referring now FIG. 4E, the face 404 is octagonal (any polygon) with an octagonal (any polygon) transducer 412 and the tubes 406 containing the fiber ends 410 surrounded by the octagonal transducer 412. The housing 402 also has an octagonal (any polygonal) cross-section and the probe 400 is octagonal solid. Of course, the probe 400 can include any shaped face and housing and any shaped transducer provided that the transducers surround the optical fibers. It should also be recognized that the transducer do not have to completely surround the optical fiber ends. Moreover, multiple transducers can be used as well.

Figure 5A:
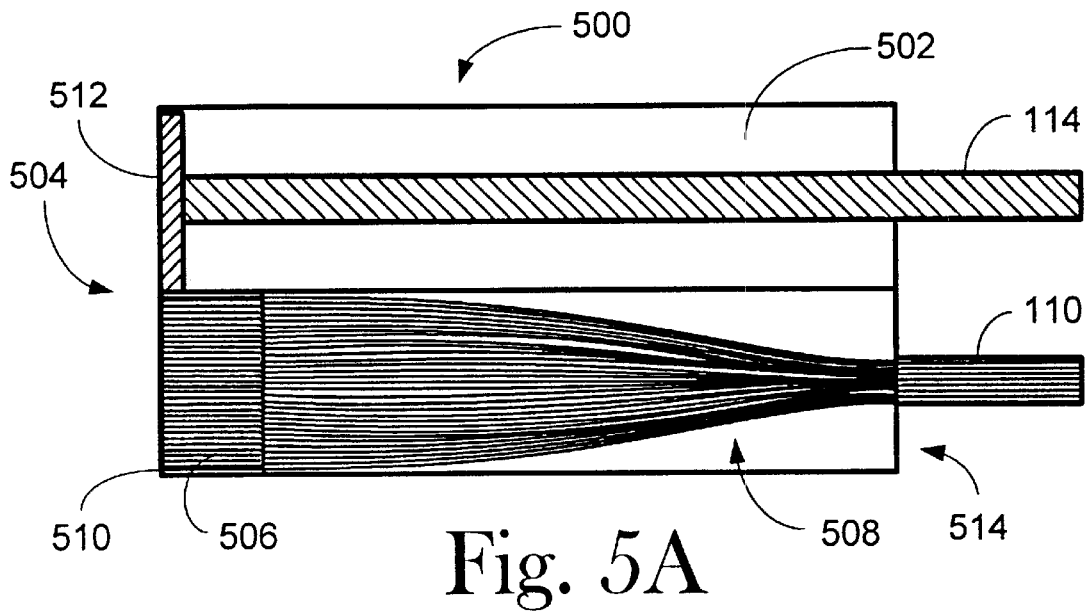
FIG. 5A depicts a cross-sectional view of another preferred embodiment of a probe with adjacent optical fiber arrays and transducers of the present invention.

Referring now to FIG. 5A, the probe 500 includes a housing 502 having a distal face 504 designed to be held in close proximity to or in contact with a body, tissue or organ site associated with a target site for which blood oxygenation data is sought. The distal face 504 includes a plurality of tubes 506 into which optical fibers 508 are inserted so that ends 510 of the optical fibers 508 are essentially flush with the face 504. The face 504 also includes a transducer 512 mounted therein so that an outer surface of the transducer 512 is also essentially flush with the face 504. The optical fibers 508 are bundled together into the optical fiber cable 110 which exits from a proximal end 514 of the probe 500. The optical cable 110 is connected to the laser output 108. The transducer 512 is connected to the electrical cable 114, which also exits the probe 500 from its proximal end 514. In distinction to the probe of FIGS. 2A–F, 3A–F and 4A–E, the probe 500 has the optical fiber ends 510 arranged adjacent to the transducer 512. Of course, the probe 500 can also include two sets of fibers from and from two different lasers as in the probes of FIGS. 3A–F.

Figure 5B:
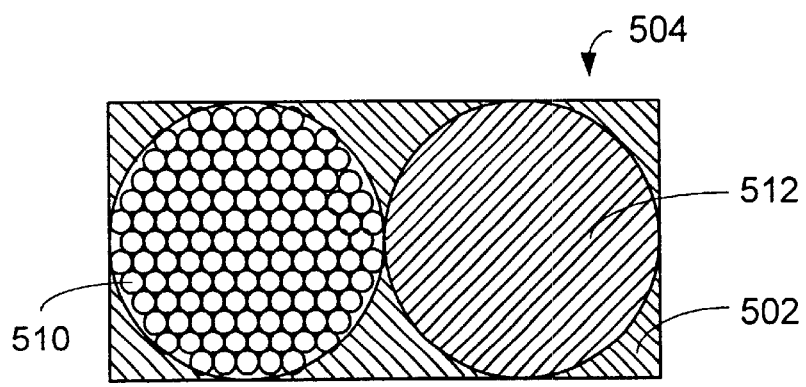
FIG. 5B depicts an end view of a face profile of the probe of FIG. 5A.
Figure 5C:
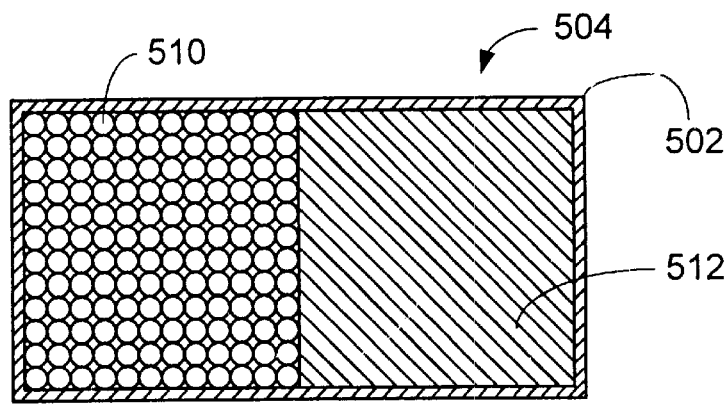
FIG. 5C depicts an end view of another face profile of the probe of FIG. 5A.

The face 504 of the probe 500 can also be arranged in a variety of different forms depending on design criteria and design choices for the final look and feel. Two illustrative examples are shown in FIGS. 5B–C. In FIG. 5B, the probe face 504 is shown to have a rectangular cross-section. Within the face 504, the tubes 506 containing the fiber 508 are situated in a first circular area 516, while the transducer 512, shown here to be circular, is situated in a second circular area 518. In FIG. 5C, the probe face 504 is shown to have a rectangular cross-section. Within the face 504, the tubes 506 containing the fiber 508 are situated in a first rectangular area 520, while the transducer 512, shown here to be rectangular, is situated in a second rectangular area 522.

FIGS. 6A–F illustrate an embodiment of the present optoacoustic blood oxygenation systems incorporating two separate probes, an acoustic probe and an irradiation probe. This embodiment allows practitioners the ability to irradiate a target tissue site at a same or different location from where acoustic sensing will be done. Thus, the two probe system allows for both forward and backward mode operation as well as modes where the irradiation and acoustic probes are at any arbitrary angle. Looking at FIG. 6A, an acoustic probe 600 includes a housing 602 having a distal face 604 designed to be held in close proximity to or in contact with a body, tissue or organ site associated with a target site for which blood oxygenation data is sought. The face 604 also includes a transducer 606 mounted therein so that an outer surface 608 of the transducer 606 is also essentially flush with the face 604. The transducer 606 is connected to the electrical cable 114, which also exits the probe 600 from its proximal end 610.

Figure 6A:
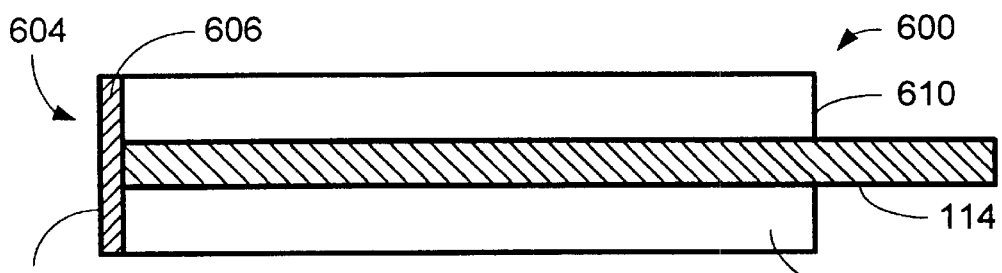
FIG. 6A depicts a cross-sectional view of an acoustic probe with a mounted transducers of the present invention.
Figure 6B:
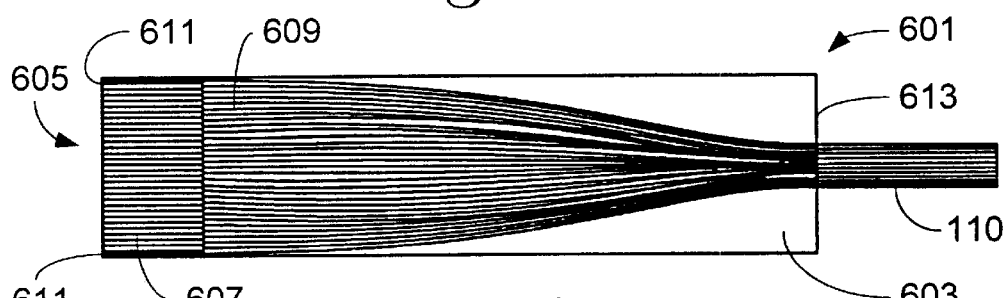
FIG. 6B depicts a cross-sectional view of an irradiation probe with mounted optical fibers of the present invention.

Looking at FIG. 6B, an irradiation probe 601 includes a housing 603 and a distal face 605 designed to be held in close proximity to or in contact with a body, tissue or organ site associated with a target site for which blood oxygenation data is sought. The face 605 includes a plurality of tubes 607 into which optical fibers 609 are inserted so that ends 611 of the optical fibers 609 are essentially flush with the face 605. The optical fibers 609 are bundled together into the optical fiber cable 110 which exits from a proximal end 613 of the probe 601. The optical cable 110 is connected to the laser output 108. Of course, the irradiation probe 601 can include one or more pluralities of optical fibers connected to different lasers.

Figure 6C:
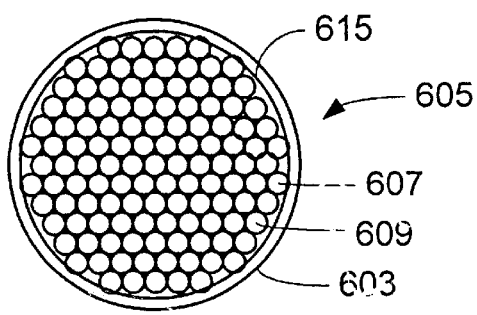
FIG. 6C depicts an end view of a face of the probe of FIG. 6A having a circular profile.
Figure 6D:
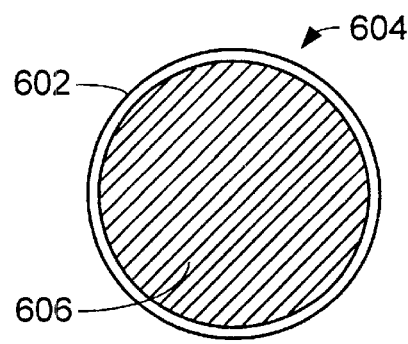
FIG. 6D depicts an end view of a face of the probe of FIG. 6B having a circular profile.
Figure 6E:
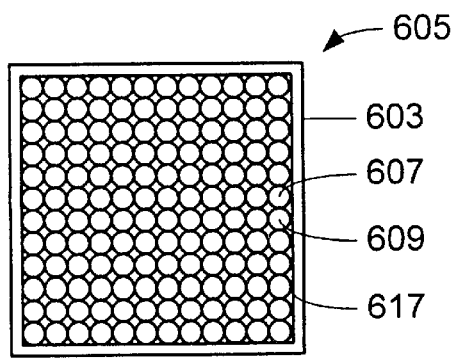
FIG. 6E depicts an end view of a face of the probe of FIG. 6A having a rectangular profile.
Figure 6F:
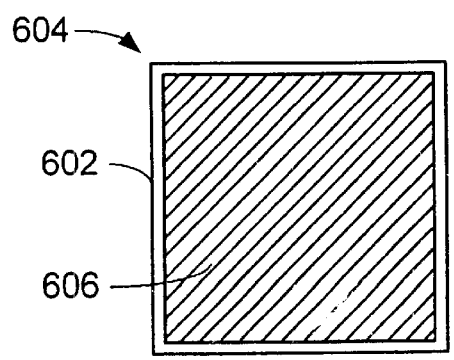
FIG. 6F depicts an end view of a face of the probe of FIG. 6B having a rectangular profile.

The probes 600 and 601 can also be arranged in a variety of different forms depending on design criteria and design choices for the final look and feel. Two illustrative examples are shown in FIGS. 6C–F. In FIGS. 6C&D, the probe faces 604 and 605 are shown to have a circular cross-section. Within the face 605, the tubes 607 containing the fiber 609 are situated in a first circular area 615, while within the face 604, a circular transducer 606 is situated. In FIGS. 6E&F, the probe faces 604 and 605 are shown to have a rectangular cross-section. Within the face 605, the tubes 607 containing the fiber 609 are situated in a rectangular area 617, while within the face 604, a rectangular transducer 606 is situated.

The optoacoustic probe is designed to irradiate blood in tissue sites or organs such as the SSS, through the skin, bond (e.g., skull), and dura and to detect the laser-induced optoacoustic waves in backward mode as shown in FIGS. 1A and B. The probe will generally include between about 12 and 144 optical fibers, preferably, between about 12 to about 60 optical fibers, particularly, between about 18 and about 48 and especially between about 18 and 36, with 24 optical fibers being most preferred. The optical fibers have diameters between about 10 $\mu$m to about 5 mm, preferably, between about 0.1 mm and 2 mm, particularly between about 0.2 mm and 1.5 mm. The probe also includes a sensitive acoustic transducer having a size controlled by the application and by design criteria. The optical fiber and transducer are preferably contained in a single housing to provide stable irradiation and detection conditions. The fibers are preferably mounted around the transducer, preferably the probe has cylindrical symmetry where light scattering in irradiated tissue provides more uniform irradiation of blood in the target tissue site such as in the SSS.

A sensitive wide-band transducer is designed to detect optoacoustic waves from blood circulating in a target tissue site such as the SSS. The choice of optimal designs of and materials for the piezoelectric element and the acoustic transducer depend on a number of parameters: bandwidth, sensitivity, acoustic impedance matching to tissues, etc. For example, polyvynylidenefluoride (PVDF) slabs is a suitable transducer for sensitive detection of optoacoustic waves from tissues. The inventors have found that a PVDF slab having a thickness between about 10 $\mu$m to about 1 mm thick. Other suitable piezoelectric materials include, without limitation, PZT, lithium niobide or other similar piezoelectric materials. The present invention can also use other pressure sensing devices such as optical devices that measure the acoustic waves optically.

An iterative approach in optimizing parameters of transducers was taken using experimental results obtained. in phantom and tissue studies. We have demonstrated that incorporation of an acoustic transducer with an electronic preamplifier on the same electronic card permits the use of a high-load resistor resulting in high sensitivity of about 3V/mbar in a wide spectral range of ultrasonic waves.

Axial resolution is defined by the transducer frequency range and is equal to about 0.3 mm for the preferred transducers. High axial resolution of the system will allow precise measurement of blood oxygenation in the target tissue site such as the SSS. High lateral resolution is not needed for the measurement of blood oxygenation in most tissue sites such as in the SSS because of its large diameter (approximately 10 mm).

In those situations were a single laser such as the preferred Nd:YAG laser, provides insufficient accuracy of blood oxygenation measurements in vivo, a second nanosecond pulsed laser can be used. For example, using a second nanosecond pulsed laser such as an Alexandrite laser ($\lambda$=750 nm), provides additional information that can improve optoacoustic measurement because deoxygenated hemoglobin has a higher absorption than oxygenated hemoglobin at this wavelength. For example, in a twenty four fiber probe, half or twelve fibers will deliver radiation from the Alexandrite laser and the half or twelve fibers will deliver radiation from the Nd: YAG laser.

Materials and Methods

Arterial and venous blood samples were taken from a sheep femoral and pulmonary artery, respectively. The artery and vein were catheterized and blood was taken using a 5 mL syringe with heparin. To obtain venous blood with very low oxygenation simulating severe hypoxia, hemorrhagic shock was induced in the sheep. A spectrophotometric cuvette with a thickness of 1 cm was used for experiments. To prevent the contact of blood with air, mineral oil was used as an air barrier fluid. Blood was injected using a syringe with a needle under the mineral oil film (thickness approximately 3 mm). The blood volume in the cuvette was 2 mL. Pure arterial and venous blood or a mixture were used in the experiments. The arterial and venous blood was mixed in the cuvette in different proportions in order to vary blood oxygenation in the cuvette. Immediately after optoacoustic data acquisition, blood was taken from the cuvette with a 1 mL syringes and oxygenation measurements were performed using a standard CO-Oximeter (IL 813 Instrumentation Laboratories, USA). Bovine bone slabs with thicknesses of about 4 to about 13 mm were used to simulate human skull in experiments to estimate transmission of laser light and optoacoustic waves through bone tissue.

A Q-switched Nd:YAG laser ($\mu$=1064 nm) (Spectra Physics, Mountain View, Calif.) with 10 ns pulse duration was employed to induce optoacoustic pressure waves in the test fluids. The energy of incident laser pulses was varied with a neutral density optical filter from about 2 to about 50 mJ. The laser beam diameter was about 8 mm, providing incident laser fluence from about 4 to about 100 mJ/cm$^2$. The pulsed laser radiation with such parameters induced an insignificant temperature increase (less than about 0.1° C.) in the samples.

Specially designed highly sensitive (about 2.5 to about 3.0 V/mbar) acoustic transducers without internal reflections were constructed and used for pressure wave (acoustic signal) detection in a wide ultrasonic spectral range from about 0.1 to about 3 MHz. These frequencies are typical of the optoacoustic waves induced in blood by irradiation with nanosecond laser pulses in the near-infrared spectral range. The pressure signals were recorded by a digital scope (TDS 520, Tektronix Inc.) and stored in a computer. Any computer can be used.

EXPERIMENTAL RESULTS

Correlation Between Optoacoustic and CO-Oximetry Measurements

Figure 7:
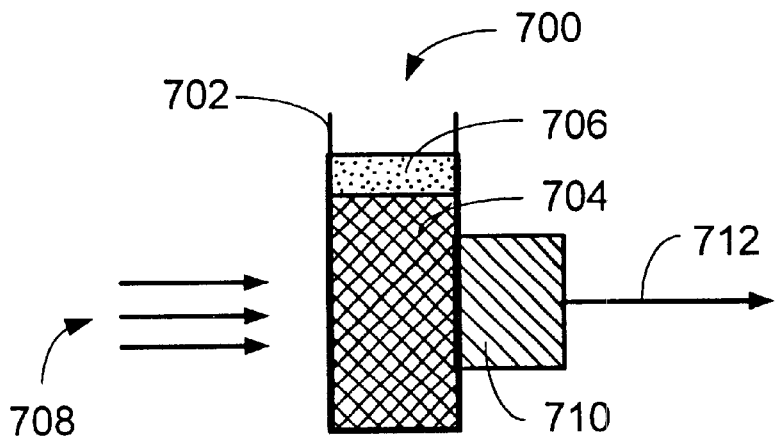
FIG. 7 depicts irradiation of blood in a cuvette with pulsed laser and detection of an acoustic signal resulting from laser pulses directed into the blood using an acoustic transducer.
Figure 8:
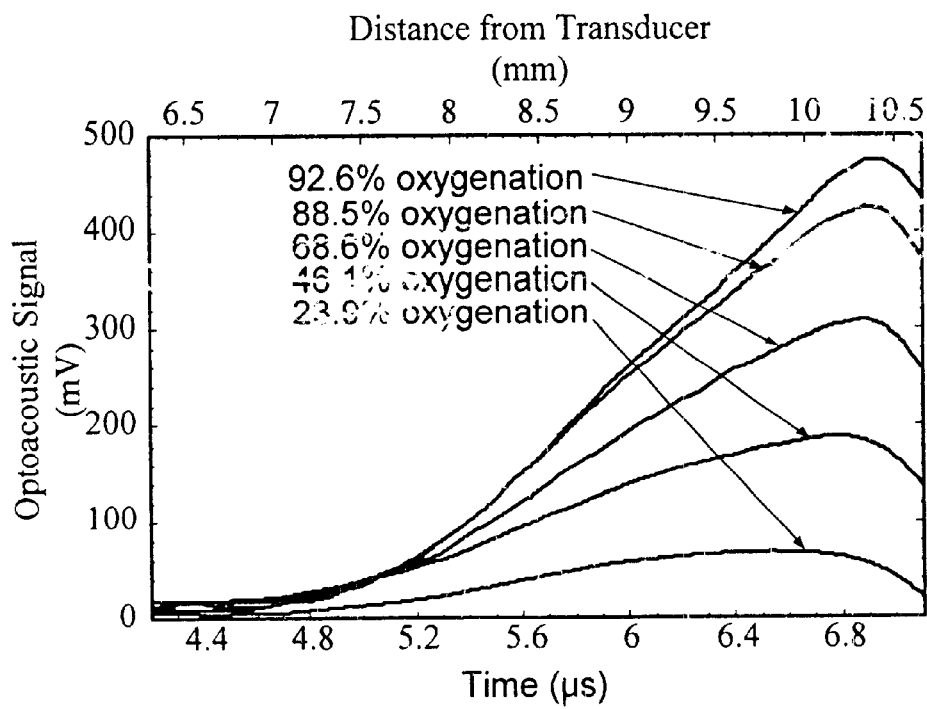
FIG. 8 graphs acoustic signal responses for blood with different oxygenation contents using data obtained from the apparatus of FIG. 5.
Figure 9:
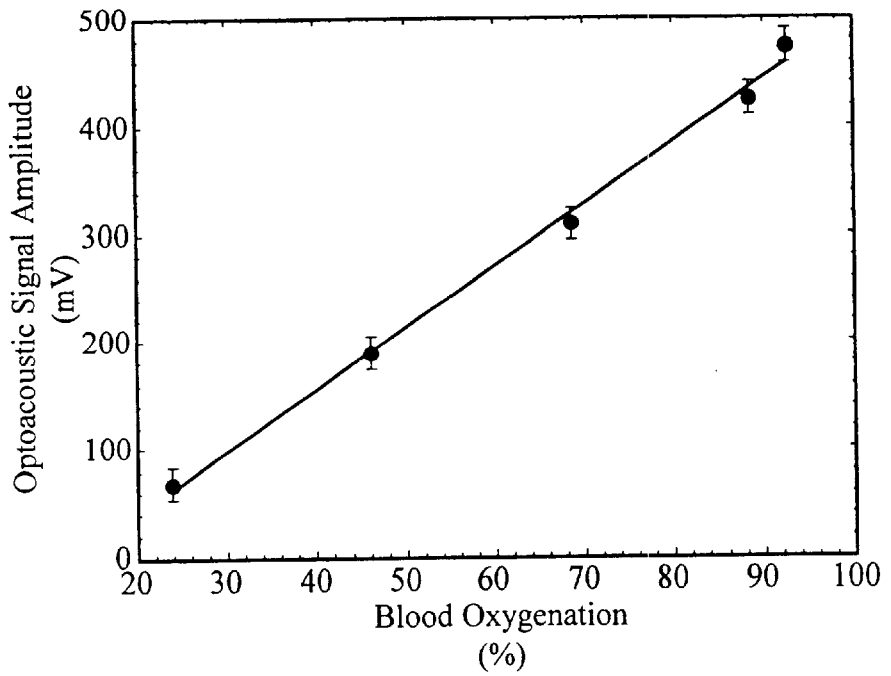
FIG. 9 graphs acoustic signal response amplitude as a function of blood oxygenation content using data obtained from the apparatus of FIG. 5.

In this example, a forward mode apparatus 700 was used comprising a cuvette 702 filled with blood 704 and covered by a layer 706 of mineral oil, which acted as an oxygen barrier as shown in FIG. 7. The blood 704 in the cuvette 702 was irradiated by laser pulses 708. Ultrasonic gel (not shown) was used to provide acoustic contact between a acoustic transducer 710 and the cuvette 702. Optoacoustic pressure waves induced in blood propagated to and are detected by the transducerproducing a corresponding output signal 712 which was recorded on a scope (not shown). The influence on optoacoustic pressure signals of changes in blood oxygenation is displayed in FIG. 8. Changes in oxygenation dramatically changed the amplitude and slope of the pressure signals. The amplitude of the optoacoustic pressure, presented in FIG. 9 as a function of blood oxygenation, increases linearly as blood oxygenation increases. The optoacoustic pressure amplitude from pure arterial blood (about 90 to about 94% saturation) was about 1.6 times greater than that from normal venous blood (about 60 to about 70% saturation). The amplitude in normal venous blood was approximately fourfold greater than in venous blood obtained during severe hemorrhagic shock (about 20 to about 30% saturation).

Figure 10:
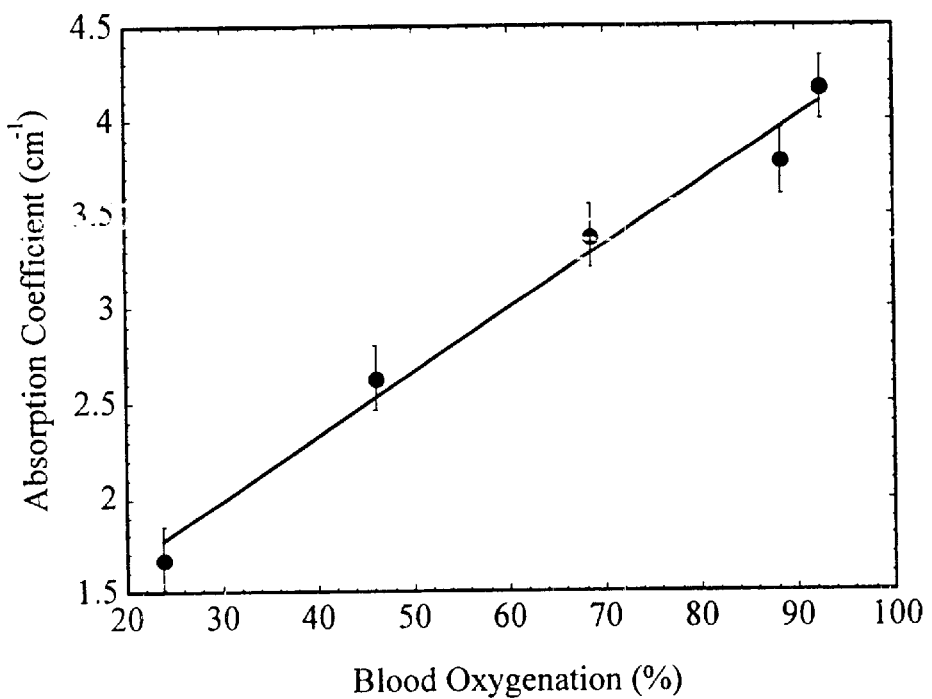
FIG. 10 graphs absorption coefficient of blood calculated from the optically induced acoustic signal responses for blood at different blood oxygenation contents using data obtained from the apparatus of FIG. 5.

In our experiment, the optoacoustic pressure slope was linearly dependent on blood oxygenation as shown in FIG. 10. The blood absorption coefficient calculated from the optoacoustic pressure signals was approximately 4.2, 3.5, and 1.8 $cm^{-1}$ for pure arterial, normal venous, and desaturated venous blood, respectively. This yields about a 20% difference in absorption coefficient between arterial and normal venous blood and about a 200% difference between normal and desaturated venous blood.

The amplitude of the pressure waves recorded from blood in vivo will depend on the thickness of the tissue between blood and transducer, diffraction of optoacoustic waves, and may vary for different patients. However, the optoacoustic pressure slope is defined only by the optical properties of blood and is not influenced by variations in tissue thickness and acoustic wave diffraction. Therefore, the optoacoustic pressure slope provides a quantitative measurement of blood oxygenation and that changes in pressure amplitude accurately reflect changes in blood oxygenation.

The inventors have thus demonstrates that optoacoustic technique can be used for accurate and absolute measurement of blood oxygenation due to the linear dependence of the optoacoustic wave parameters on blood oxygenation.

Continuous Optoacoustic Monitoring of Blood Oxygenation

Figure 11:
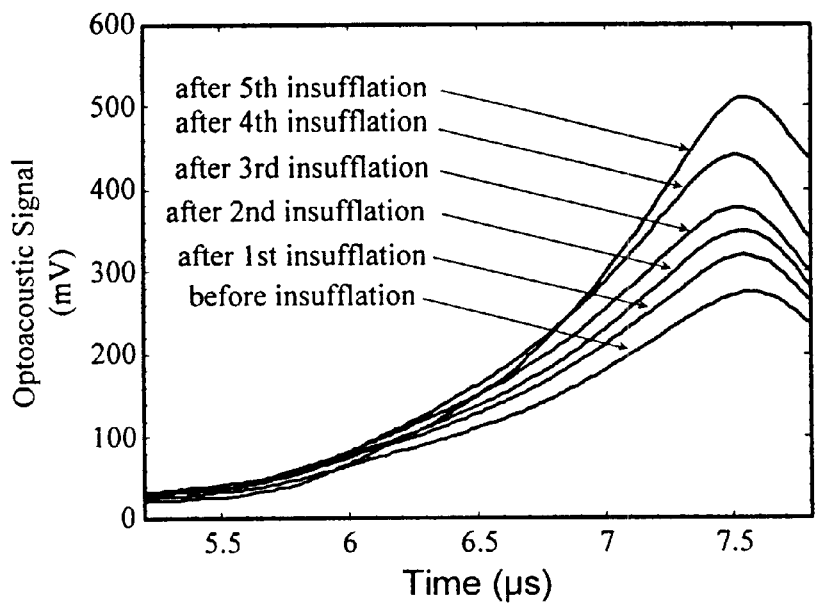
FIG. 11 graphs optically induced acoustic signal responses from blood before and after insufflation of air.
Figure 12:
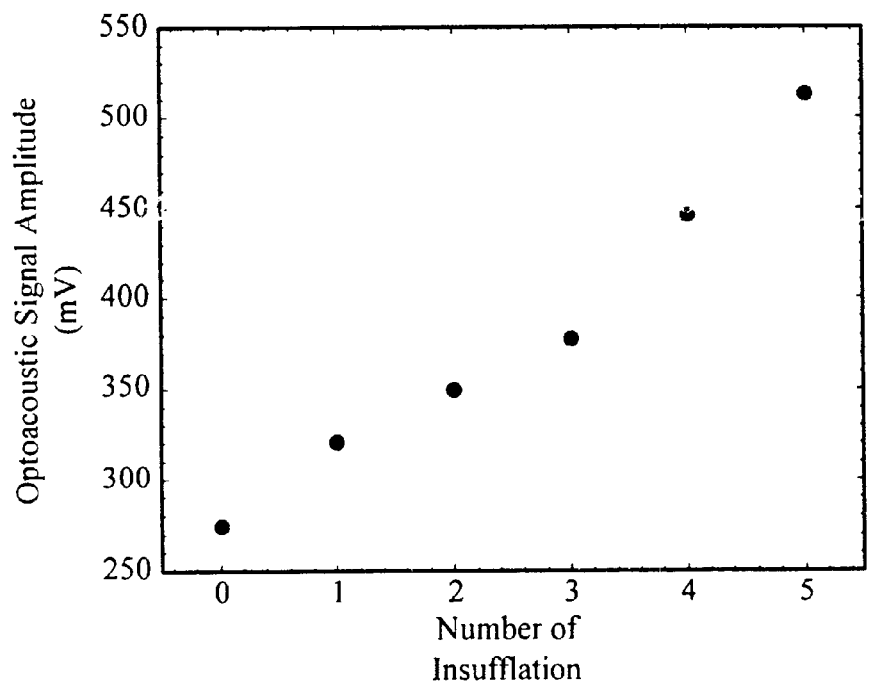
FIG. 12 graphs amplitude of optoacoustic signal response in blood before and after insufflation of air.

The inventors have also demonstrated the capability of optoacoustic technique to continuously monitor rapid changes in blood oxygenation in real time. The changes in oxygenation were induced by insufflation of air through venous blood in the cuvette. The insufflation increased blood oxygenation. The optoacoustic signals as shown in FIG. 11 changed with insufflation. FIG. 12 shows that the optoacoustic amplitude increases from values typical of venous blood (about 260 mV) to that typical of arterial blood (about 500 mV). The delay between the optoacoustic data acquisitions (several seconds) was limited by the time required for insufflation. The optoacoustic data acquisition and processing can be performed every second. This optoacoustic system was used for real-time monitoring of rapid changes in tissue temperature as well as changes in optical properties during coagulation [49–51]. Therefore, blood oxygenation can be measured every second with the optoacoustic technique.

These results show that (1) blood oxygenation can be monitored continuously and (2) that rapid changes (within seconds) in blood oxygenation can be detected with the optoacoustic technique.

Optical and Acoustic Transmission Through Bone

Figure 13:
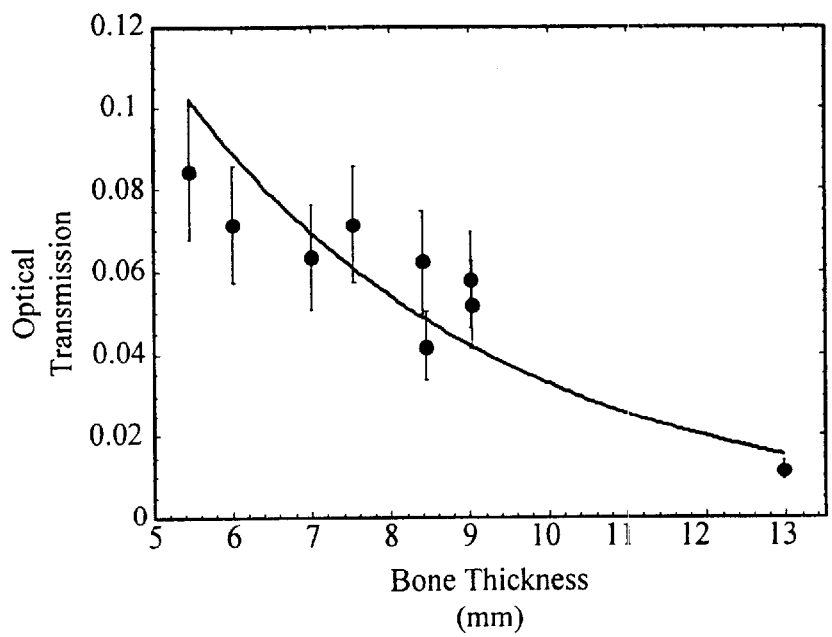
FIG. 13 graphs optical transmission through bone samples of different thickness.
Figure 14:
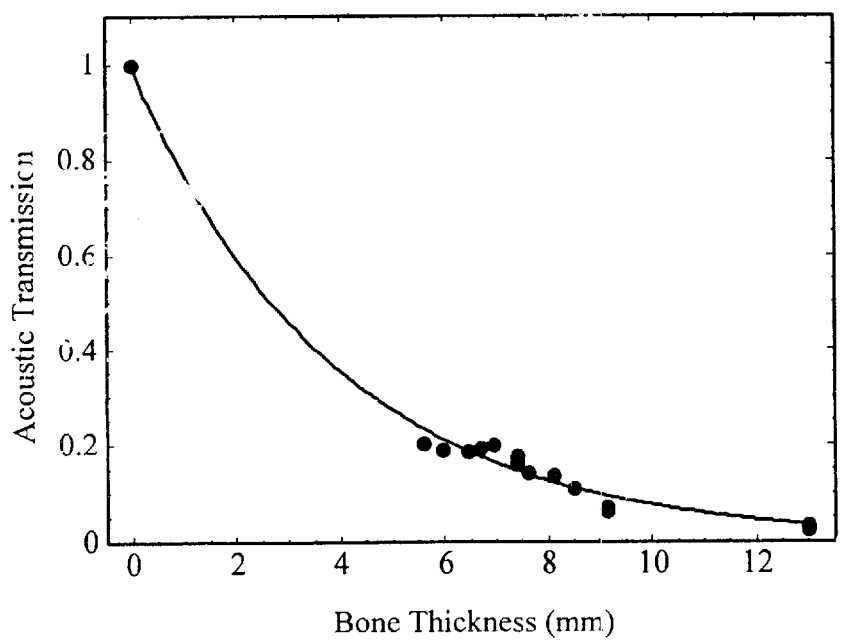
FIG. 14 graphs transmission of optically induced acoustic waves (signal responses) through bone samples of different thickness.

Transmission of pulsed Nd:YAG laser radiation with the wavelength of $\lambda$=1064 nm is presented in FIG. 13 as a function of bone thickness. The curve represents an exponential fit of the experimental data points. These results show that about 3% of pulse energy is transmitted through bone of 10-mm thickness. The error in the data points is caused by variation in the optical properties of the bone samples. Experiments on transmission of optoacoustic pressure waves through bone as shown in FIG. 14 showed that at he amplitude decreases by a factor of 12.5 times at a bone thickness of 10 mm compared with amplitude of the incident pressure wave. Therefore, approximately 8% attenuation of optoacoustic pressure amplitude can be expected in the skull.

Figure 15:
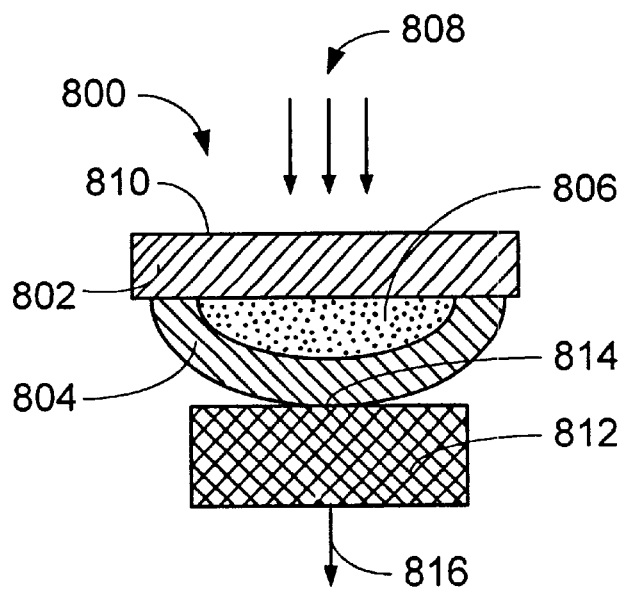
FIG. 15 depicts irradiation and detection of optically induced acoustic waves from an absorbing solution simulating venous blood through two bones.
Figure 16:
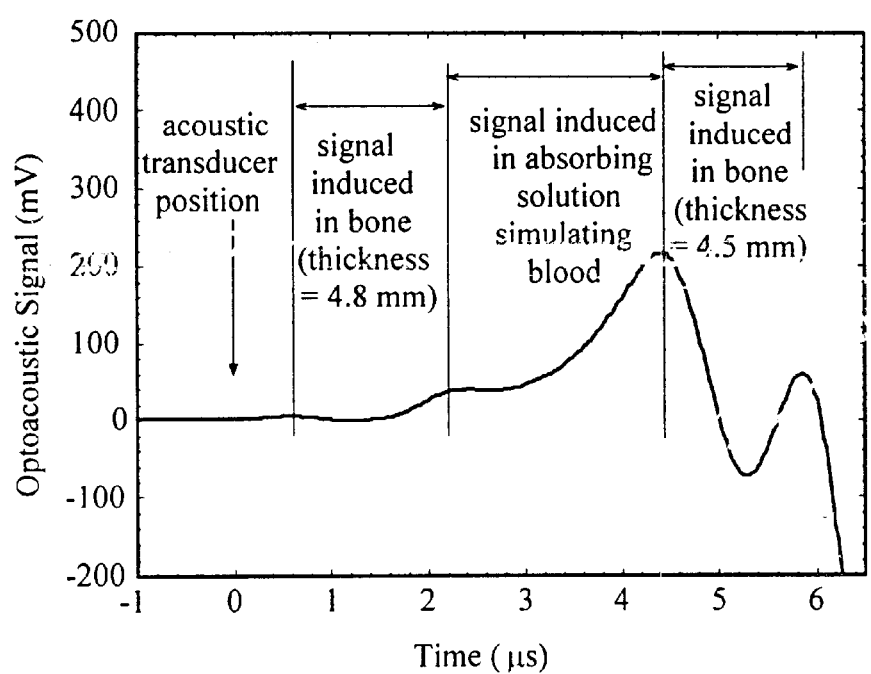
FIG. 16 graphs optoacoustic signal recorded from absorbing solution simulating venous blood in the SSS.

To simulate laser irradiation of blood and detection of the induced optoacoustic signal through bone in a forward mode apparatus of this invention as shown in FIG. 15, the apparatus 800 comprised a top substantially flat bone fragments 802 and a bottom upwarded curved bone fragment 804. The upward curved bone fragment 804 is filled with an absorbing solution 806 simulating venous blood in the SSS. Laser pulses 808 irradiated a top surface 810 of the top bone fragment 802 and a transducer 812 placed in contact with a lower surface 814 of the bottom bone fragment 804 to receive induced acoustic waves generated in the solution 810 by the pulses 808. The transducer output 816 was forwarded to a scope (not shown). The solution 806 had optical properties typical of normal venous blood. A signal with an amplitude of about 200 mV was detected at the energy of laser pulse of 5 mJ as shown FIG. 16. Noise level of the registration system was 0.5 mV.

The skin and dura are thin and will have optical and acoustic attenuation substantially less than the skull. Therefore, these data demonstrate that optoacoustic signals with a high signal-to-noise ratio can be induced in blood in the SSS and can be measured non-invasively.

Experiment with Novel Optoacoustic Probe of FIG. 1

A novel optoacoustic probe was designed, built, and tested. The probe allowed detection of optoacoustic waves induced in tissues. The probe had PVDF piezoelectric element (transducer) with a diameter of 8 mm and 200-$\mu$m optical fibers around it. The fibers were arranged in a bundle at the input (laser) end. The signals induced in the samples by laser pulses were detected by the sensitive transducer, amplified by a standard amplifier, and recorded by a digital scope with a computer. This design allowed irradiation and detection of optoacoustic waves from the same side of the samples and can be used for non-invasive monitoring of blood oxygenation in vivo.

A Q-switched Nd:YAG laser ($\lambda$=1064 nm) with the pulse duration of 10 ns was used as a source of pulsed optical radiation in the near IR spectral range. Tissue phantoms were irradiated by the laser pulses with the energy of about 10 mJ.

FIG. 17 shows optoacoustic signal recorded from a gelatin slab with the thickness of 15 mm and optical properties typical for tissues in the near IR spectral range (absorption coefficient=0.11 $cm^{-1}$, reduced scattering coefficient=2.9 $cm^{-1}$, effective attenuation coefficient=1.0 $cm^{-1}$). The first sharp peak was produced by optoacoustic wave generation on the surface of the probe. The second (wide) peak with the following negative part was detected from the turbid gelatin. This optoacoustic signal is typical for uniform media.

To simulate blood circulating under a turbid tissue, a layered tissue phantom was used. The first 9-mm layer was made of the same turbid gelatin. The second layer was made of gelatin with higher absorption coefficient (5 $cm^{-1}$) typical for blood in the near IR spectral range. The optoacoustic probe was placed on the surface of the turbid gelatin. The signal recorded from the layered phantom has one more peak as shown in FIG. 18. This peak was produced in the absorbing gelatin.

These experiments demonstrate that the optoacoustic probe is capable of detection of optoacoustic waves in the backward mode (irradiation and detection of optoacoustic waves from the same side) from absorbing objects through thick turbid media and can potentially be used for non-invasive monitoring of blood oxygenation.

Different designs of the optoacoustic probe can be used for this application. For instance, the fibers can be placed in the center of the probe, while a pressure sensing device surrounding the optical fibers will have a narrow angle of acceptance that may provide higher lateral resolution and, hence, greater sensitivity of optoacoustic pressure wave detection from blood vessels.

The fibers and piezoelectric element can be just simply mounted close to each other in one probe. In this case, there will be no axial symmetry of pressure waves detection as in the two previous probes, however this design is simple and may provide accuracy and sensitivity needed for oxygenation monitoring.

Experiment with Pump Oxygenator

The system used to test the feasibility of an optoacoustic system to monitor oxyhemoglobin saturation (or blood oxygenation) was a commercially available pump oxygenator (cardiopulmonary bypass machine). This system consists of a reservoir in which blood accumulates, a supply of gases (oxygen, carbon dioxide, and nitrogen), a membrane oxygenator, an "arterial" line (which in patients would be inserted into the aorta), a rotary pump, and a "venous" line (which in patients would return blood from the great veins in the chest). In this model, the arterial and venous lines are simply connected through a monitoring phantom (which replicates features of tissue through which a vessel courses) to form a complete ex vivo circuit. By changing the gas supply into the membrane oxygenator and permitting time for equilibration, the oxyhemoglobin saturation can be adjusted over a broad range and also can be changed in random order. For instance, changing the gas supply to 95% oxygen results in nearly complete oxyhemoglobin saturation; changing the gas supply to 5% oxygen results in oxyhemoglobin saturation of approximately 50%. Changing the gas supply below 5% provides oxyhemoglobin saturation below 50%.

In our experiments, oxyhemoglobin saturation was varied between 100% and about 10%. FIG. 19 shows optoacoustic signals recorded from blood circulating through a 5-mm latex tube simulating a blood vessel. The tube was embedded in a phantom simulating tissue between the optoacoustic probe and the vessel. The signals were recorded through a 5-mm turbid gelatin slab (50 cm×50 cm) with optical properties typical for tissues in the near IR spectral range (absorption coefficient=0.11 cm$^{-1}$, reduced scattering coefficient=2.9 cm$^{-1}$, effective attenuation coefficient=1.0 cm$^{-1}$) and a plastic cuvette with 7-mm walls. FIG. 19 shows optoacoustic pressure signals recorded from the phantom at different blood oxygenation: 100%, 44%, 27%, and 10%. Fresh sheep blood was used in these experiments. Blood samples (1 mL) were taken simultaneously with the optoacoustic data Acquisition and blood oxygenation was measured with a standard CO-Oxymeter (IL 813 Instrumentation Laboratories, USA).

The first sharp peak was produced by generation of optoacoustic waves directly on the surface of the optoacoustic probe. The long signal with the wide maximum at 2.4 $\mu s$ was due to optoacoustic wave generation in the turbid gelatin. The signal between 5 and 8 $\mu s$ was generated in blood circulating in the tube. It is clearly seen that the parameters of the signal are dependent on blood oxygenation. The amplitude and slope of the signal increase with the increase of blood oxygenation due to higher absorption coefficient of oxyhemoglobin compared with that of deoxyhemoglobin. These experiments demonstrate capability of the optoacoustic technique to detect changes in blood oxygenation continuously, non-invasively, and in real time through a tissue-like turbid medium by with the optoacoustic probe in the forward mode.

REFERENCES

1. Prough D S, Yancy V, Deyo D J. Brain monitoring. Considerations in patients with craniocerebral missile wounds. In Aarabi B., Kaufman H. H. (eds): Missile Wounds of the Head and Neck. The American Association of Neurosurgical Surgeons: 221–53, 1999.
2. Cruz J. Miner M E, Allen S J, Alves W M, Gennarelli T A. Continuous monitoring of cerebral oxygenation in acute brain injury: injection of mannitol during hyperventilation. Journal of Neurosurgery. 73(5):725–30, 1990.
3. Cruz J. The first decade of continuous monitoring of jugular bulb oxyhemoglobin saturation: management strategies and clinical outcome. Crit Care Med. 26:344–51, 1998.
4. Robertson C S, Simpson R K, Jr. Neurophysiologic monitoring of patients with head injuries. Neurosurg. Clin.N.Am.2:285–99, 1991.
5. Gopinath S P, Robertson C S, Contant C F, et al. Jugular venous desaturation and outcome after head injury. J. Neurol. Neurosurg. Psychiatry. 57:717–23, 1994.
6. Marion D W, Darby J, Yonas H. Acute regional cerebral blood flow changes caused by severe head injuries. J. Neurosurg. 74:407–14, 1991.
7. Marion D W, Bouma G J. The use of stable xenon-enhanced computed tomographic studies of cerebral blood flow to define changes in cerebral carbon dioxide vasoresponsivity caused by a severe head injury. Neurosurgery. 29:869–73, 1991.
8. Bouma G J, Muizelaar J P, Choi S C, et al: Cerebral circulation and me tabolism after severe traumatic brain injury: the elusive role of ischemia. J. Neurosurg. 75: 685–93, 1991.
9. Bouma G J, Muizelaar J P, Stringer W A, et al. Ultra-early evaluation of regional cerebral blood flow in severely head-injured patients using xenon-enhanced computerized tomography. J. Neurosurg. 77:360–68, 1992.
10. Newman M F. Croughwell N D. Blumenthal J A. White W D. Lewis J B. Smith L R. Frasco P. Towner E A. Schell R M. Hurwitz B J. et al. Effect of aging on cerebral autoregulation during cardiopulmonary bypass. Association with postopertive cognitive dysfunction. Circulation. 90(5 Pt 2):II243–9, 1994.
11. Newman M F, Croughwell N D, White W D, et al. Effect of perfusion pressure on cerebral blood flow during normothermic cardiopulmonary bypass. Circulation 94, II353–357, 1996.
12. Murkin J M. Farrar J K. Tweed W A. McKenzie F N. Guiraudon G. Cerebral autoregulation and flow/metabolism coupling during cardiopulmonary bypass: the influence of PaCO2. Anesthesia & Analgesia. 66(9):825–32, 1987.
13. Murkin J M. Lee D H. Noninvasive measurement of cerebral blood flow: techniques and limitations [editorial; comment]. Canadian Journal of Anaesthesia. 38(7):805–8, 1991.

14. Rogers A T. Prough D S. Stump D A. Gravlee G P. Angert K C. Roy R C. Mills S A. Hinshelwood L. Cerebral blood flow does not change following sodium nitroprusside infusion during hypothermic cardiopulmonary bypass. Anesthesia & Analgesia. 68(2): 122–6, 1989.
15. Levin H S. Goldstein F C. High W M Jr. Eisenberg H M. Disproporti onately severe memory deficit in relation to normal intellectual functioning after closed head injury. Journal of Neurology, Neurosurgery & Psychiatry. 51(10):1294–301, 1988.
16. Prough D S. Rogers A T. Stump D A. Roy R C. Cordell A R. Phipps J. Taylor C L. Cerebral blood flow decreases with time whereas cerebral oxygen consumption remains stable during hypothermic cardiopulmonary bypass in humans [see comments]. Anesthesia & Analgesia. 72(2):161–8, 1991.
17. Croughwell N D. Frasco P. Blumenthal J A. Leone B J. White W D. Reves J G. Warming during cardiopulmonary bypass is associated with jugular bulb desaturation. Annals of Thoracic Surgery. 53(5):827–32, 1992.
18. Croughwell N D. Newman M F. Blumenthal J A. White W D. Lewis J B. Frasco P E. Smith L R. Thyrum E A. Hurwitz B J. Leone B J. et al. Jugular bulb saturation and cognitive dysfunction after cardiopulmonary bypass [see comments]. Annals of Thoracic Surgery. 58(6):1702–8, 1994.
19. Zauner A. Doppenberg E M. Woodward J J. Choi S C. Young H F. Bullock R. Continuous monitoring of cerebral substrate delivery and clearance: initial experience in 24 patients with severe acute brain injuries. Neurosurgery. 41(5):1082–91; discussion 1091–3, 1997.
20. Wray S., M. Cope, D. T. Deply, J. S. Wyatt, and E. O. R. Reynolds. "Characterization of the near infrared absorption spectra of cytochrome $aa_3$ and hemoglobin for the non-invasive monitoring of cerebral oxygenation", Biochim. et Biophys. Acta, 1988; vol. 933, pp. 184–192.
21. Welch A J, Van Gemert M J C, Optical-thermal response of laser-irradiated tissue, New York: Plenum Press, 1995.
22. Pollard V. Prough D S. DeMelo A E. Deyo D J. Uchida T. Stoddart H F. Validation in volunteers of a near-infrared: spectroscope for monitoring brain oxygenation in vivo. Anesthesia & Analgesia. 82(2):269–77, 1996.
23. Pollard V. Prough D S. DeMelo A E. Deyo D J. Uchida T. Widman R. The influence of carbon dioxide and body position on near-infrared spectroscopic assessment of cerebral hemoglobin oxygen saturation. Anesthesia & Analgesia. 82(2):278–87, 1996.
24. Pollard V. Prough D S. Cerebral oxygenation: near-infrared spectroscopy. In Tobin M J (ed): Principles and Practice of Intensive Care Monitoring. New York, McGraw-Hill, Inc.:1019–33, 1988.
25. Chance B. Leigh J S. Miyake H. Smith D S. Nioka S. Greenfeld R. Finander M. Kauftnann K. Levy W. Young M. et al. Comparison of time-resolved and -unresolved measurements of deoxyhemoglobin in brain. Proceedings of the National Academy of Sciences of the United States of America. 85(14):4971–5, 1988.
26. Kirkpatrick P J. Smielewski P. Whitfield P C. Czosnyka M. Menon D. Pickard J D. An observational study of near-infrared spectroscopy during carotid endarterectomy [see comments]. Journal of Neurosurgery. 82(5):756–63, 1995.
27. Levy W J. Levin S. Chance B. Near-infrared measurement of cerebral oxygenation. Correlation with electroencephalographic ischemia during ventricular fibrillation. Anesthesiology. 83(4):738–46, 1995.
28. Newman M F, Lowry E, Croughwell N D, et al. Near-infrared spectroscopy (INVOS 3100 A) and cognitive outcome after cardiac surgery. Anesth. Analog. 84:S1–S599, 1997.
29. Patterson M S, Chance B, Wilson B C. Time resolved reflectance and transmittance for the non-invasive measurement of tissue optical properties. Applied Optics. 28:2331–36,1989.
29B. Q. Zhu, E. Conant, B. Chance: Optical imaging as an adjunct to sonograph in differentiating benign from malignant breast lesions, J. Biomed. Opt. 2000; vol. 5 (2), pp. 229–236.
30. A. A. Oraevsky, S. L. Jacques, F. K. Tittel: Determination of tissue optical properties by time-resolved detection of laser-induced stress waves. Proc. SPIE 1993; 1882: 86–101 and Esenaliev R.O., Oraevsky A.A., Letokhov V.S., Karabutov A.A., Malinsky T.V. Studies of Acoustical and Shock Waves in the Pulsed Laser Ablation of Biotissue. Lasers Surg. Med., 1993, v.13, pp.470–484.
31. Oraevsky A. A., Jacques S. L., Esenaliev R. O., Tittel F. K. Imaging in layered tissues using time-resolved detection of laser-induced stress transients. SPIE Proc. 1994, v. 2134, pp. 122–128.
32. Oraevsky A. A., Esenaliev R. O., Jacques S. L., Tittel F. K. Laser opto-acoustic tomography for medical diagnostics: principles. SPIE Proc. 1996, v. 2676, pp. 22–31.
33. Esenaliev R. O., Oraevsky A. A., Jacques S. L., Tittel F. K. Laser opto-acoustic tomography for medical diagnostics: Experiments wtih biological tissues. SPIE Proc. 1996, v. 2676, pp. 84–90.
34. Oraevsky A. A., Esenaliev R. O., Jacques S. L., Tittel F. K. Laser Optoacoustic tomography for breast cancer diagnostics, In: "Trends in Optics and Photonics", vol. II, ed. by R R Alfano and J G Fujimoto, OSA Publishing House, pp. 316–321 (1996).
35. Oraevsky A. A., Esenaliev R. O., Karabutov A. A. Optoacoustic Imaging in Layered Tissues: Signal Processing. SPIE Proc. 1997, v. 2979, pp. 59–70.
36. Esenaliev R. O., Karabutov A. A., Tittel F. K., Fornage B. D., Thomsen S. L., Stelling C., Oraevsky A. A. Laser Optoacoustic Imaging for Breast Cancer Diagnostics: Limit of Detection and Comparison with X-ray and Ultrasound Imaging. SPIE Proc. 1997, v. 2979, pp. 71–82.
37. Esenaliev R. O., Alma H., Tittel F. K., Oraevsky A. A. Axial resolution of laser optoacoustic imaging: Influence of acoustic attenuation and diffraction. SPIE Proc. 1998, v. 3254, pp. 294–301.
38. Esenaliev R O, Karabutov A A, Oraevsky A A. Sensitivity of Laser Opto-Acoustic Imaging for Detection of Early Breast Cancer. Journal of Quantum Electronics, v.5(4),1999, In press.
39. Oraevsky A. A., Andreev V. G., Karabutov A. A., and Esenaliev R. O. Two-Dimensional Opto-Acoustic Tomography Transducer Array and Image Reconstruction Algorithm. SPIE Proc. 3601:256–267, 1999.
40. Oraevsky A. A, Andreev V. G., Karabutov A. A., Fleming D. R., Gatalica Z., Singh H., and Esenaliev R. O. Laser Opto-Acoustic Imaging of the Breast: Detection of Cancer Angiogenesis. SPIE Proc. 3597, 1999, In press.
41. A. A. Oraevsky, S. L. Jacques, R. O. Esenaliev. "Optoacoustic Imaging for Medical Diagnostics". U.S. Pat. No. 5,840,023 issued Nov. 4, 1998.
42. Esenaliev R. O., Oraevsky A. A., Motamedi M., Karabutov A. A. "Real-time Optoacoustic Monitoring of Changes in Tissue Properties" U.S. patent application Ser. No. 09/412,852 filed Oct. 21, 1999.
43. Esenaliev R. O., Motamedi M. M, Prough D. S., Oraevsky A. A. "Optoacoustic Monitoring of Blood Oxygenation." U.S. Provisional Patent Application No. 60/147, 577 filed Aug. 6, 1999.

44. Gusev V. E., Karabutov A. A. "Laser Optoacoustics", AIP Press, New York, 1993.
45. Clifton G L, Allen S, Barrodale P, et al: A phase II study of moderate hypothermia in severe brain injury. J.Neurotrauma. 10:263–271, 1993.
46. Marion D W, Penrod L E, Kelsey S F, et al: Treatment of traumatic brain injury with moderate hypothermia. N.Engl.J.Med. 336:540–546, 1997.
47. Perinatal and infant brain imaging: role of ultrasound and computed tomography. Carol M. Rumack, Michael L. Johnson. Chicago: Year Book Medical Publishers, 1984.
48. Ultrasound and the fetal brain. edited by F. A. Chervenak, A. Kurjak, and C. H. Comstock. New York: Parthenon Pub. Group, 1995.
49. Esenaliev R. O., Oraevsky A. A., Larin K. V., Larina I. V., Motamedi M. Real-Time Optoacoustic Monitoring of Temperature in Tissues. SPIE Proc. 3601:268–275, 1999.
50. Esenaliev R. O., Larin K. V., Larina I. V., Motamedi M., Oraevsky A. A. Optical properties of normal and coagulated tissues: Measurements using combination of optoacoustic and diffuse reflectance techniques. SPIE Proc. 1998, v. 3726, pp. 560–566.
51. Esenaliev R. O., Larina I. V., Larin K. V, Motamedi M, Karabutov A A, Oraevsky A A. Laser Optoacoustic Technique for Real-Time Measurement of Thermal Damage in Tissues. SPIE Proc. 3594, 1999, In press.
52. Bland J M, Altman D J. Statistical methods for assessing agreement between two methods of clinical measurement. The Lancet, 8:307–10, 1986.
53. Nowak R. D. and Baraniuk R. G. "Wavelet-based nonlinear signal and image processing", In: Wavelet Applications in Signal and Image Processing IV, M. A. Unser; A. Aldroubi, and A. F. Laine, Eds., Proc. SPIE vol. 2825: 260–271, 1996.
54. American National Standard for Safe Use of Lasers. ANSI Z136.1–1993.

All references cited herein are incorporated by reference. While this invention has been described fully and completely, it should be understood that, within the scope of the appended claims, the invention may be practiced otherwise than as specifically described, Although the invention has been disclosed with reference to its preferred embodiments, from reading this description those of skill in the art may appreciate changes and modification that may be made which do not depart from the scope and spirit of the invention as described above and claimed hereafter.

We claim:
1. An optoacoustic apparatus comprising:
a pulsed laser;
an optical delivery system connected to an output of the pulsed laser and adapted to deliver pulsed radiation to a target site of an animal including a human; and
an acoustic sensing system adapted to be placed in close proximity to or in contact with the target site and to receive an acoustic signal induced in the target site by the pulsed radiation, where the acoustic signal is time resolved and a slope of the time resolved acoustic signal represents a quantitative measure of blood oxygenation in the target site and changes in an amplitude of the time-resolved acoustic signal represents a measure of changes in blood oxygenation in the target site.
2. The apparatus of claim 1, further comprising a digital processing unit in electrical communication with the acoustic sensing system and adapted to convert an acoustic sensing system output signal into the measure of blood oxygenation in the target site and a probe comprising the optical delivery system and the acoustic sensing system, where the probe is adapted to provide irradiation conditions between the target site and the optical delivery system and acoustic contact between the target site and the acoustic sensing system sufficient to permit detection of induced pressure waves in the target site due to the pulsed optical from the optical delivery system.
3. The apparatus of claim 1, wherein the pulsed laser generates pulses of relatively short duration at a wavelength between about 600 nm and about 1400 nm.
4. The apparatus of claim 1, wherein the optical delivery system terminates in an irradiation probe having a distal face adapted to be placed in close proximity to or in contact with the target site and the acoustic sensing system comprises a transducer having sufficient sensitivity, temporal resolution, and bandwidth to detect a pressure profile induced in the the target site due to the pulsed radiation and mounted in a distal face of an acoustic probe and an acoustic cable connected to the transducer, where the cable is adapted to supply power to the transducer and to carry the acoustic signal from the transducer.
5. The apparatus of claim 1, where the optical delivery system terminates in a distal face of a probe and the acoustic sensing system comprises a transducer having sufficient sensitivity, temporal resolution, and bandwidth to detect a pressure profile induced in a tissue or vessel by the pulsed radiation and mounted in the distal face of the probe and an acoustic cable connected to the transducer, where the cable is adapted to supply power to the transducer and to carry the acoustic signal from the transducer.
6. The apparatus of claim 5, wherein the optical delivery system comprises a plurality of optical fibers having ends that terminate in or on the distal face of the probe.
7. The apparatus of claim 6, wherein the ends of the optical fibers are arranged adjacent the transducer.
8. The apparatus of claim 6, wherein the ends of the optical fibers partially or completely surround the transducer.
9. The apparatus of claim 6, wherein the transducer partially or completely surrounds the ends of the optical fibers.
10. The apparatus of claim 1, wherein the target site comprise a heart tissue, a pulmonary artery, an aorta, an artery or vein in a neck or an artery or vein in a brain, and the quantitative measure of blood oxygenation is used to detect or monitor a stroke or to detect or monitor changes in blood oxygenation in a brain tissue, a superior sagittal sinus, an intracerebral vessel, a jugular bulb, a liver tissue, a portal vein, a kidney tissue, or a kidney vein or artery.
11. The apparatus of claim 1, wherein irradiation of the target site by the pulsed radiation and detection of the induced acoustic signal in the target site are performed on a same or different surface of the target site.
12. The apparatus of claim 1, wherein the target site comprises an internal organ and wherein the pulsed radiation is delivered endoscopically and the acoustic sensing system is in close proximity to or in contact with an exterior surface of the target site.
13. The apparatus of claim 1, wherein the target site comprises an internal organ and wherein the pulsed irradiation is delivered at an exterior surface of the animal body including a human body and wherein the acoustic sensing system is positioned endoscopically in close proximity to or in contact with an interior surface of the target site.
14. The apparatus of claim 1, wherein the target site comprises an internal organ and wherein a distal end of the optical delivery system and a distal end of the acoustic sensing system are incorporated in an optoacoustic probe and wherein the probe is positioned inside the organ, so that irradiation and detection are performed from a same internal surface of the organ.

15. The apparatus of claim 1, wherein the target site comprises a tumor and wherein quantitative measure of blood oxygenation is sufficient to differentiate between a malignant tumor and a benign tumor.

16. The apparatus of claim 1, wherein the target site is a cardiac chamber.

17. A probe including a front face having mounted thereon a transducer connected to an output cable and a plurality of optical fibers terminating at or in the front face, where light from a radiation source sent down the fibers exits the probe at the face and enters a tissue site of an animal including a human causing an acoustic response which is detected by the transducer causing the transducer to generate a time resolved output signal, where a slope of the time resolved data output signal represents a quantitative measure of blood oxygenation and changes in an amplitude of the time-resolved output signal represents a measure of changes in blood oxygenation in the target site.

18. An optoacoustic apparatus comprising:
a first pulsed radiation source;
a first fiber-optics delivery system including a first plurality of optical fibers, where the system is connected to an output of the first radiation source at its proximal end;
a probe including a face having a transducer mounted therein and adapted to receive the first fiber-optics delivery system, where distal ends of the first plurality of optical fibers terminate at or near the face of the probe;
a transducer cable connected, at its proximal end, to the transducer and adapted to supply power to the transducer and carry a transducer output signal from the transducer; and
a digital processing unit connected to a distal end of the transducer cable adapted to time resolve the transducer output signal and to convert a slope of the time resolved transducer output signal into a quantitative measure of blood oxygenation and to convert changes in an amplitude of the time-resolved transducer output signal into a measure of changes in blood oxygenation in the target site.

19. The apparatus of claim 18, further comprising:
a second pulsed radiation source and a second fiber-optics delivery system including a second plurality of optical fibers,
where the second fiber-optics delivery system is connected to an output of the second pulsed radiation source at its proximal end and the second plurality of optical fibers terminate at or near the face of the probe and wherein the first pulsed radiation source comprises a Nd:YAG laser, the second pulsed radiation source comprises an Alexandrite laser and the pulses from both lasers have a relatively short pulse duration.

20. The apparatus of claim 19, wherein the distal ends of the first and second plurality of optical fibers partially or completely surround the transducer, the transducer partially or completely surrounds the distal ends of the first and second plurality of optical fibers or the ends of the optical fibers are adjacent to the transducer.

21. A probe including a front face having mounted thereon a transducer connected to an output cable that exits a back portion of the probe, a first and second plurality of optical fibers terminating at or in the front face of the probe, where light from a first radiation source sent down the first plurality fibers and light from a second radiation source sent down the second plurality of fibers and exit the probe at the face and enters a tissue of an animal including a human causing a time resolved acoustic response which causes the transducer to generate an output signal, where a slope of the time resolved data output signal represents a quantitative measure of blood oxygenation and changes in an amplitude of the time-resolved output signal represents a measure of changes in blood oxygenation in the target site.

22. A method for measuring blood oxygenation comprising the steps of:
directing radiation pulses from a pulsed radiation source into a target site of an animal including a human;
receiving acoustic or pressure waves induced in the target site by the pulsed radiation;
generating an output signal corresponding to the received acoustic waves, where a slope of the output signal is linearly related to blood oxygenation and changes in the amplitude of the output signal is linearly related to changes in blood oxygenation; and
converting the output signal into a measure of blood oxygenation and changes in blood oxygenation in the target site.

23. The method of claim 22, further comprising the step of:
displaying the measure of blood oxygenation or changes in blood oxygenation on a display device.

24. The method of claim 22, wherein the measure of blood oxygenation is performed intra-operatively on open brain tissue, superior sagittal sinus, myocardium, or other exposed tissue or blood vessel.

25. The method of claim 22, wherein absorbing dyes sensitive to blood oxygenation are used to provide higher accuracy of the measure of blood oxygenation.

* * * * *